United States Patent
Hodson et al.

(10) Patent No.: US 7,825,113 B2
(45) Date of Patent: *Nov. 2, 2010

(54) 2-OXY-BENZOXAZINONE DERIVATIVES FOR THE TREATMENT OF OBESITY

(75) Inventors: Harold Francis Hodson, Beckenham (GB); Robert Downham, Cambridge (GB); Timothy John Mitchell, Cambridge (GB); Beverley Jane Carr, Royston (GB); Christopher Robert Dunk, Ely (GB); Richard Michael John Palmer, Hayes (GB)

(73) Assignee: Norgine B.V., Amsterdam (NL)

( * ) Notice: Subject to any disclaimer, the term of this patent is extended or adjusted under 35 U.S.C. 154(b) by 977 days.

This patent is subject to a terminal disclaimer.

(21) Appl. No.: 10/306,377

(22) Filed: Nov. 27, 2002

(65) Prior Publication Data

US 2003/0195206 A1      Oct. 16, 2003

Related U.S. Application Data

(60) Division of application No. 09/901,887, filed on Jul. 6, 2001, now Pat. No. 6,624,161, which is a continuation of application No. PCT/GB00/00032, filed on Jan. 6, 2000.

(30) Foreign Application Priority Data

| Jan. 8, 1999 | (GB) | ................................. 9900413.7 |
| Jul. 22, 1999 | (GB) | ................................. 9917294.2 |

(51) Int. Cl.
A61K 31/535      (2006.01)

(52) U.S. Cl. .................................................. 514/230.5
(58) Field of Classification Search ............... 514/230.5
See application file for complete search history.

(56) References Cited

U.S. PATENT DOCUMENTS

| 4,657,893 | A |   | 4/1987 | Krantz et al. ................... 514/18 |
| 4,665,070 | A |   | 5/1987 | Krantz et al. ................... 514/232 |
| 4,745,116 | A |   | 5/1988 | Krantz et al. ................... 514/230.5 |
| 5,776,756 | A | * | 7/1998 | Kimura et al. ................... 435/189 |
| 6,624,161 | B2 | * | 9/2003 | Hodson et al. ................... 514/230.5 |

FOREIGN PATENT DOCUMENTS

| DE | 246 996 | 6/1987 |
| DE | 246996 | 6/1987 |
| EP | 0206323 | 12/1986 |
| WO | WO96/07648 | 3/1996 |
| WO | WO99/16758 | 4/1999 |

OTHER PUBLICATIONS

Hays et al. "2-Amino-4H-3,1-benzoxazin-4-ones as inhibitors of C1r Serine Protease" *J. Med Chem.* 1998, 41, 1060-1067.
Krantz et al. "Design and Synthesis of 4H-3,1-Benzoxazin-4-ones as Potent Alternative Substrate Inhibitors of Human Leukocyte Elastase" *J. Med Chem.* 1990, 33, 464-479.
Krantz et al. "Design of Alternate Substrate Inhibitors of Serine Proteases. Synergistic Use of Alkyl Substitution to Impede Enzyme-Catalyzed Deacvlation" *J. Med. Chem.* 1987, 30 (4), 589-590.
Krantz et al. "Design of Alternate Substrate Inhibitors of Serine Proteases: Tactics for Obstructing Deacylation Pathways" *Advances in Biosciences* 1987. 65. 213-220.
Neumann et al. "Inhibition of Chymotrypsin and Pancreatic Elastase by 4H-3,1-Benzoxazin-4-ones" *J. Enzvme Inhibition*, 1991, 4, 227-232.
Gutschow et al. "Inhibition of Cathepsin G by 4H-3,1-Benzoxazin-4-ones" *Bioorg. Med. Chem.* 1997, 5, 1935-1942.
Jarvest et al. "Inhibition of HSV-1 Protease by Benzoxazinones" *Bioorg. Med. Chem.* 1996, 6, 2463-2466.
PCT/GB00/00032; International Search Report mailed Dec. 12, 2000.

* cited by examiner

*Primary Examiner*—Alton N Pryor
(74) *Attorney, Agent, or Firm*—Choate, Hall & Stewart LLP; Charles E. Lyon; John P. Rearick

(57) ABSTRACT

The use of a compound comprising formula (I):

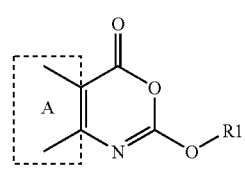

(I)

or a salt, ester, amide or prodrug thereof in the inhibition of an enzyme whose preferred mode of action is to catalyse the hydrolysis of an ester functionality, e.g. in the control and inhibition of unwanted enzymes in products and processes. The compounds are also useful in medicine e.g. in the treatment of obesity and related conditions. The invention also relates to novel compounds within formula (I), to processes for preparing them and pharmaceutical compositions containing them.

In formula (I) A is a 6-membered aromatic or heteroaromatic ring; and $R^1$ is a branched or unbranched alkyl (optionally interrupted by one or more oxygen atoms), alkenyl, alkynyl, cycloalkyl, cycloalkenyl, aryl, arylalkyl, reduced arylalkyl, arylalkenyl, heteroaryl, heteroarylalkyl, heteroarylalkenyl, reduced aryl, reduced heteroaryl, reduced heteroarylalkyl or a substituted derivative of any of the foregoing groups.

23 Claims, No Drawings

2-OXY-BENZOXAZINONE DERIVATIVES FOR THE TREATMENT OF OBESITY

PRIORITY INFORMATION

This application is a divisional application of U.S. Ser. No. 09/901,887, filed on Jul. 6, 2001 now U.S. Pat. No. 6,624,161. U.S. Ser. No. 09/901,887 is in turn a continuation of international application number PCT/GB00/00032, filed on Jan. 6, 2000, entitled "2-Oxy-Benzoxazinone Derivatives for the Treatment of Obesity", which PCT application claims priority to GB 9900413.7, filed on Jan. 8, 1999, and GB 9917294.2, filed on Jul. 22, 1999, and the entire contents of each of these is hereby incorporated by reference.

The present invention provides known and novel compounds, their use in the inhibition of an enzyme whose preferred mode of action is to catalyse the hydrolysis of an ester functionality (in vivo, as the enzyme naturally occurs) their use in medicine, and particularly in the prevention and/or treatment of obesity or an obesity-related disorder. Also provided are methods for the prevention and/or treatment of obesity or an obesity-related disorder and for promoting/aiding non-medical weight loss and the use of the compounds in the manufacture of a medicament for the aforementioned indications. In respect of novel compounds the invention also provides processes for their manufacture, compositions containing them and methods for manufacturing such compositions.

In the last 20 years, there has been an increasing trend in obesity in the populations of the developed world. The increased incidence of obesity is due in part to the ready availability of food in numerous retail outlets and westernised diets that have high saturated fat and lower fibre contents such that the food is energy dense. The lifestyle of the populations of the developed world has also become more sedentary with the increased mechanisation of society and the steady reduction of manual labour intensive industries. There now exists an energy imbalance between the energy intake from calorie dense foods and the reduced energy expenditure required for a sedentary lifestyle. Some of the excess energy intake is stored as fat in the adipose tissue, the accumulation of which over a period of time results in obesity and can be a significant contributory factor to other disease and disorders.

Obesity is now recognised by the medical profession as a metabolic disease. In the USA, it is estimated that 25% of the adult population is considered clinically obese (Body Mass Index>30). Obesity can be a debilitating condition which reduces the quality of life and increases the risk of related disorders such as diabetes, cardiovascular disease and hypertension. It has been estimated that $45 billion of US healthcare costs, or 8% per annum of total healthcare spend, is as a direct result of obesity. The traditional approaches to long term weight management such as diet and exercise have proved ineffective alone to control the spread of obesity. Today, more than ever, there is considerable interest in developing safe, effective drugs for the treatment of obesity.

Pharmacological approaches to the treatment of obesity have focused on either developing drugs that increase energy expenditure or drugs that reduce energy intake. One approach to the reduction of energy intake is to reduce the body's ability to digest and absorb food, in particular fat. The key enzymes involved in the digestion of fat are hydrolytic enzymes. The most significant of the fat degrading enzymes are lipases, primarily, but not exclusively pancreatic lipase that is secreted by the pancreas into the gut lumen. The lipase inhibitor lipstatin has formed the basis of the anti-obesity drug, orlistat. Orlistat is the subject of published European Patent Application No. EP129748, which relates to compounds of formula:

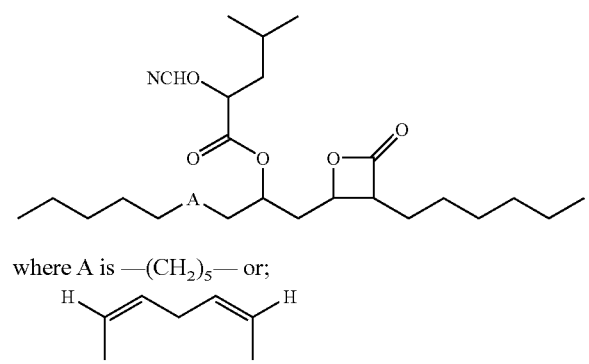

where A is —$(CH_2)_5$— or;

and their use in inhibiting pancreatic lipase and treating hyperlipaemia and obesity. Orlistat has as its major active moiety a beta-lactone group that reacts to form an ester with the side chain hydroxyl group of serine 152 within the active site of pancreatic lipase.

Even if orlistat provides an effective method for treating obesity, there remains a need to provide alternative drugs and methods for use in the control and treatment of obesity and obesity-related disorders and in promoting or aiding non-medical weight loss. Inhibitors of enzymes involved in the degradation of fat are provided here and shown to be effective in the prevention and/or treatment of obesity, obesity-related disease and/or in promoting cosmetic weight loss.

U.S. Pat. No. 4,665,070 (Syntex) describes a broad class of 2-oxy-4H-3,1-benzoxazin-4-ones of the formula:

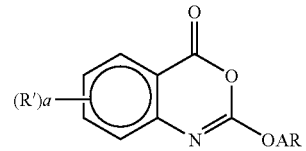

where a is an integer from 0-4; each R' may be selected from a wide range of substituents; A is a bond or a $C_{1-8}$ alkylene group; and R is H (except when A is a bond) phenyl, imidazolyl or $C_{3-6}$ cycloalkyl each of which rings may be optionally substituted. The R' groups are said to be preferably in the 5- and/or 7-positions of the ring. A preferred value of the group A is lower alkylene having 1-4 carbon atoms. In the most preferred compounds A is ethylene. The compounds are said to be useful as serine protease inhibitors and to treat physiologic conditions and disease states known to involve enzymes, or as contraceptives. The specification describes various conditions and diseases involving enzymatic pathways, including inflammation, arthritis, tumor cell metastasis, pulmonary emphysema, mucocutaneous lymph node syndrome, adult respiratory distress syndrome and pancreatitis. It is also suggested that the compounds may have antiparasitic, anticoagulant and/or antiviral activity. Similar compounds are also described in U.S. Pat. No. 4,745,116.

International Patent Application No. WO89/07639 (BP Chemicals Ltd) describes detergent compositions in aqueous solution which comprise a surfactant, a precursor compound capable of giving rise to a peroxygen compound in the presence of water, a suds suppressing agent, a detergent builder and a bleach activator which may have the formula:

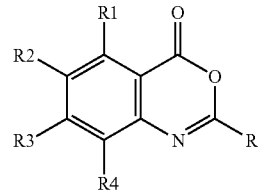

where R is inter alia an alkoxy group and $R^1$, $R^2$, $R^3$ and $R^4$ (which may be the same or different) are selected from H, halogen, alkyl, alkenyl, aryl, hydroxyl, alkoxyl, amino, alkylamino, —$COOR^5$ and carbonyl functions. The number of carbon atoms in the alkyl groups and moieties is not defined, but the specific examples are of lower alkyl and alkoxy groups e.g. R may be ethoxy.

East German Patent No. DD 246996A1 describes a process for preparing 2-alkoxy- and 2-aryloxy-3,1-benzoxazin-4-ones of the formula:

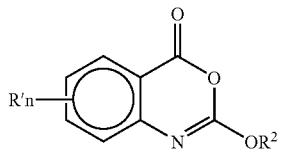

where $R'_n$ represents one or more H atoms and/or other substituents such as alkyl, alkoxy, aralkyl, aryl, thiocyanato, mercapto, alkylthio, halogen or nitro, and $R^2$ represents an alkyl, aralkyl or aryl residue. The compounds are said to be useful as herbicides and fungicides and to have activity as inhibitors of chymotrypsin. Specific examples of $R^2$ are ethyl, benzyl and phenyl.

We have now found that a particular class of benzoxazinone compounds has activity as lipase inhibitors.

Accordingly, in a first aspect, the present invention provides the use of a compound comprising formula (I):

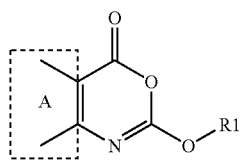

(I)

or a pharmaceutically acceptable salt, ester, amide or prodrug thereof; in the manufacture of a medicament for the treatment of conditions which require the inhibition of an enzyme whose preferred mode of action is to catalyse the hydrolysis of an ester functionality, wherein in formula (I):
A is a 6-membered aromatic or heteroaromatic ring; and
R' is a branched or unbranched alkyl (optionally interrupted by one or more oxygen atoms), alkenyl, alkynyl, cycloalkyl, cycloalkenyl, aryl, arylalkyl, reduced arylalkyl, arylalkenyl, heteroaryl, heteroarylalkyl, heteroarylalkenyl, reduced aryl, reduced heteroaryl, reduced heteroarylalkyl or a substituted derivative of any of the foregoing groups, wherein the substituents are one or more independently of halogen, alkyl, halosubstituted alkyl, aryl, arylalkyl, heteroaryl, reduced heteroaryl, reduced heteroarylalkyl, arylalkoxy, cyano, nitro, —$C(O)R^4$, —$CO_2R^5$, —$SOR^4$, —$SO_2R^4$, —$NR^6R^7$, $OR^6$, —$SR^6$, —$C(O)CX^1X^2NR^6R^7$, —$C(O)N(OH)R^6$, —$C(O)NR^5R^4$, —$NR^6C(O)R^4$, —$CR^6(NH_2)CO_2R^6$, —$NHCX^1X^2 CO_2R^6$, —$N(OH)C(O)NR^6R^7$, —$N(OH)C(O)R^4$, —$NHC(O)NR^6R^7$, —$C(O)NHNR^6R^7$, —$C(O)N(OR^5)R^6$, or a lipid or steroid (natural or synthetic) with the proviso that any hetero atom substituent in $R^1$ must be separated from the exocyclic oxygen atom by at least two carbon atoms (preferably saturated);

and where:—
$R^4$ is hydrogen, alkyl, alkenyl, alkynyl, cycloalkyl, cycloalkenyl, aryl, arylalkyl, heteroaryl, heteroarylalkyl, reduced heteroaryl, reduced heteroarylalkyl, —$OR^6$, —$NHCX^1X^2CO_2R^6$ or —$NR^6R^7$;
$R^5$ is hydrogen, alkyl, alkenyl, alkynyl, cycloalkyl, cycloalkenyl, aryl, arylalkyl heteroaryl, heteroarylalkyl, reduced heteroaryl or reduced heteroarylalkyl; and $R^6$ and $R^7$ are independently hydrogen, alkyl, alkenyl, alkynyl, cycloalkyl, cycloalkenyl, aryl, arylalkyl, heteroaryl, reduced heteroaryl, reduced heteroarylalkyl or —$(CH_2)n(OR^5)m$ wherein n is 1 to 12, preferably 2 to 10, wherein m is 1-3 and $R^5$ is most preferably $C_2$-$C_{10}$ alkyl; and $X^1$ and $X^2$ are independently hydrogen, alkyl, alkenyl, alkynyl, cycloalkyl, cycloalkenyl, aryl, beteroaryl, arylalkyl, heteroarylalkyl, reduced heteroaryl or reduced heteroarylalkyl.

In compounds of formula (I) any alkyl, alkenyl and alkynyl groups and moieties may be straight chain (unbranched) or branched chain. Straight chain alkyl, alkenyl and alkynyl groups or moieties may contain from 1 to 30 carbon atoms, eg. 1 to 25 carbon atoms, preferably 1 to 20 carbon atoms. Branched chain alkyl, alkenyl and alkynyl groups or moieties may contain from 1 to 50 carbon atoms, preferably 1 to 30 carbon atoms.

Preferred values for $R^1$, $R^4$, $R^5$, $R^6$, $R^7$, $X^1$ and $X^2$ are as defined below for formulae (II) and (IIa). In particular, preferred values for $R^4$, $R^5$ and $R^6$ are as defined for $R^{13}$ hereinbelow and preferred values for $R^7$ are as defined for $R^{14}$ hereinbelow.

In this text, 'reduced', in the context of 'reduced heteroaryl' and the like means fully or partially saturated.

Aryl groups include for example optionally substituted unsaturated monocyclic or bicyclic rings of up to 12 carbon atoms, such as phenyl and naphthyl, and partially saturated bicyclic rings such as tetrahydro-naphthyl. Examples of substituents which may be present on an aryl group include one or more of halogen, amino, nitro, alkyl, haloalkyl, alkoxy, phenoxy and phenoxy substituted by one or more of halo, alkyl or alkoxy.

A heteroaryl group or moiety may be for example an optionally substituted 5- or 6-membered heterocyclic aromatic ring which may contain from 1 to 4 heteroatoms selected from O, N and S. The heterocyclic ring may optionally be fused to a phenyl ring. Examples of heteroaryl groups thus include furyl, thienyl, pyrrolyl, oxazolyl, oxazinyl, thiazolyl, imidazolyl, oxadiazolyl, thiadiazolyl, pyridyl, triazolyl, triazinyl, pyridazyl, pyrimidinyl, pyrazolyl, indolyl, indazolyl, benzofuranyl, benzothienyl, benzimidazolyl, benzoxazolyl, benzoxazinyl, quinoxalinyl, quinolinyl, quinazolinyl, cinnolinyl, benzothiazolyl, pyridopyrrolyl. Suitable substituents include one or more of halogen, oxo, amino, nitro, alkyl, haloalkyl, alkoxy, phenoxy and phenoxy substituted by one or more of halo, alkyl, haloalkyl or alkoxy.

A reduced heteroaryl group or moiety may be for example a fully or partially saturated derivative of the aforementioned heteroaryl groups. Examples of reduced heteroaryl groups thus include pyrrolidinyl, tetrahydrofuryl, tetrahydrothienyl and piperidinyl.

The compounds of formula (I) are useful inhibitors of enzymes involved in the degradation of fats. Preferably therefore the first aspect of the invention provides the use of a compound of formula (I) as defined hereinabove, or a pharmaceutically acceptable salt, ester, amide or prodrug thereof, in the manufacture of a medicament for the control or treatment of obesity, or obesity-related disorders or for promoting non-medical weight loss.

Preferably, a compound for use according to the first aspect of the invention is a compound of formula (II):

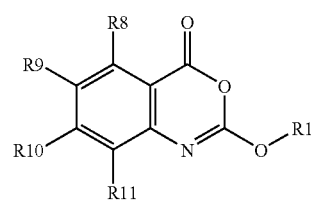

(II)

or a pharmaceutically acceptable salt, ester, amide or prodrug thereof, wherein:—
$R^1$, $R^4$, $R^5$, $R^6$, $R^7$, $X^1$ and $X^2$ are as defined above for formula (I); and
$R^8$, $R^9$, $R^{10}$, $R^{11}$ are each independently hydrogen, halo, hydroxy, amino, nitro, cyano,
or a group $R^1$, as defined above,
or a group $R^{12}Q$ where Q is O, CO, CONH, NHCO, S, SO, $SO_2$, or $SO_2NH_2$ and $R^{12}$ is hydrogen or a group $R^1$ as defined above,
or a group $R^1R^2N$ where $R^1$ is as defined above and $R^2$ is hydrogen or $R^1$, with the proviso that any hetero atom substituent in $R^1$ and/or $R^2$ must be separated from the aromatic hetero atom substituent by at least two carbon atoms (preferably saturated). Preferred values of $R^1$, $R^8$, $R^9$, $R^{10}$ and $R^{11}$ are as defined below for compounds of formula (IIa).

More preferably, a compound for use according to the first aspect of the invention comprises a compound of formula (II), or a pharmaceutically acceptable salt, ester, amide or prodrug thereof; wherein:
$R^1$ is either a branched or unbranched alkyl group having up to 25, e.g. up to 20 carbon atoms, an aryl (e.g. optionally substituted phenyl or 2-naphthyl), an arylalkyl group wherein the alkyl moiety has up to 25, e.g. up to 20 carbon atoms, or an aryl aryl group, wherein the aryl alkyl group or the aryl aryl group may be separated by a spacer, and where the spacer can be one or more of an ester, amide, O, $CH_2$ or a ketone and wherein any aryl group is preferably a phenyl, optionally substituted with alkyl, haloalkyl or halogen;
$R^8$ is hydrogen or fluorine;
$R^9$ is lower branched or unbranched alkyl having 1 to 10 carbon atoms, preferably methyl; cyclic alkyl having 3 to 10 carbon atoms, preferably cyclopropyl; haloalkyl, preferably trifluoromethyl; or a halogen, most preferably chlorine or fluorine;
$R^{10}$ is hydrogen lower branched or unbranched alkyl having 1 to 10 carbon atoms, preferably methyl; cyclic alkyl having 3 to 10 carbon atoms, preferably cyclopropyl; haloalkyl, preferably trifluoromethyl; or a halogen, most preferably chlorine or fluorine;
$R^{11}$ is hydrogen lower branched or unbranched alkyl having 1 to 10 carbon atoms, preferably methyl, or halogen, preferably fluorine.

In particular, $R^1$ is an unbranched alkyl group, having 12, 14, 15, 16, 17 or 18 carbon atoms in the alkyl chain. In addition to this particular option for $R^1$, $R^9$ may be methyl.

In a second aspect the present invention provides novel compounds of formula (IIa):

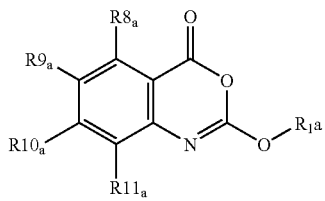

(IIa)

or a pharmaceutically acceptable salt, ester, amide or prodrug thereof; where:
$R^{1a}$ is
(i) a $C_{10-30}$ branched or unbranched alkyl, optionally substituted by one or more independently of $C_{3-6}$ cycloalkyl, $C_{3-6}$ cycloalkenyl, aryl, heteroaryl, reduced heteroaryl, —C(O)$R^{13}$, —CO$_2R^{13}$, —SO$_2R^{13}$, —SO$_2R^{13}$, —NR$^{13}R^{14}$, —OR$^{13}$, —SR$^{13}$, —C(O)NR$^{13}R^4$, —NR$^{14}$C(O)$R^{13}$, halogen, cyano, and nitro and/or optionally interrupted by one or more oxygen atoms with the proviso that any hetero atom in $R^1$ must be separated from the exocyclic oxygen atom (or from any other heteroatom) by at least two carbon atoms (preferably saturated);

(ii) $C_{2-25}$ alkenyl, $C_{2-25}$ alkynyl, $C_{3-6}$ cycloalkenyl, aryl-$C_{2-25}$ alkenyl, heteroaryl-$C_{2-25}$alkenyl, reduced heteroaryl, reduced heteroaryl-$C_{1-25}$ alkyl or a substituted derivative of any of the foregoing groups wherein the substituents are one or more independently of $C_{1-6}$ alkyl, halosubstituted $C_{1-6}$ alkyl, aryl, aryl-$C_{1-6}$ alkyl, heteroaryl, reduced heteroaryl, reduced heteroaryl-$C_{1-6}$ alkyl, $C_{1-6}$ alkoxy, aryl-$C_{1-6}$alkoxy, —C(O)$R^{13}$, —CO$_2R^{13}$, —SOR$^{13}$, —SO$_2R^{13}$, —NR$^{13}R^{14}$, —OR$^{13}$, —SR$^{13}$, —C(O)NR$^{13}R^{14}$, —NR$^4$C(O)$R^{13}$, halogen, cyano, and nitro, with the proviso that any hetero atom in $R^1$ must be separated from the exocyclic oxygen atom (or from any other heteroatom) by at least two carbon atoms (preferably saturated);

(iii) a $C_{1-9}$ alkyl group interrupted by one or more oxygen atoms and optionally substituted by one or more independently of $C_{3-6}$ cycloalkyl, $C_{3-6}$ cycloalkenyl, aryl, heteroaryl, reduced heteroaryl, —C(O)$R^3$, —CO$_2R^{13}$, —SOR$^{13}$, —SO$_2R^{13}$, NR$^{13}R^{14}$, OR$^{13}$, SR$^{13}$, —C(O)NR$^{13}R^{14}$, —NR$^{14}$C(O)$R^{13}$, halogen, cyano and nitro with the proviso that any hetero atom in $R^1$ must be separated from the exocyclic oxygen atom (or from any other heteroatom) by at least two carbon atoms (preferably saturated); or (iv) a $C_{1-9}$ alkyl group substituted by a group selected from —C(O)$R^{13}$, —CO$_2R^{13}$, SOR$^{13}$, SO$_2R^{13}$, NR$^{13}R^{14}$, OR$^{13}$, SR$^{13}$, C(O)NR$^{13}$ $R^{14}$, NR$^{14}$C(O)$R^{13}$; halogen, cyano, nitro, bicyclic aryl, bicyclic heteroaryl, monocyclic or bicyclic reduced heteroaryl, and monocyclic heteroaryl other than imidazolyl;

(v) a phenyl group substituted by a group selected from OR$^{17}$, —COR$^{13}$, —CO$_2R^{13}$, SOR$^{13}$, SO$_2R^{13}$, CONR$^{13}R^{14}$, NR$^{14}$C(O)$R^{13}$; halosubstituted $C_{1-6}$ alkyl, aryl, aryl$C_{1-6}$alkyl, heteroaryl and heteroaryl$C_{1-6}$alkyl; or (vi) a bicyclic aryl, bicyclic heteroaryl, monocyclic or bicyclic reduced heteroaryl, or monocyclic heteroaryl group other than imidazolyl, optionally substituted by a group selected from OR$^{17}$, —COR$^{13}$, —CO$_2R^{13}$, SOR$^{13}$, SO$_2R^{13}$, CONR$^{13}R^{14}$, NR$^{14}$C(O)$R^{13}$; halosubstituted $C_{1-6}$ alkyl, aryl, aryl$C_{1-6}$alkyl, heteroaryl and heteroaryl$C_{1-6}$alkyl;

where $R^{13}$ and $R^{14}$ each independently represents hydrogen, $C_{1-10}$alkyl, $C_{2-10}$alkenyl, $C_{2-10}$alkynyl, $C_{3-6}$cycloalkyl, $C_{3-6}$cycloalkenyl, aryl, aryl$C_{1-10}$ alkyl, heteroaryl, heteroaryl$C_{1-10}$alkyl, reduced heteroaryl or reduced heteroaryl, $C_{1-10}$alkyl, and $R^{17}$ represents hydrogen or $C_{2-10}$alkenyl, $C_{2-10}$alkynyl, $C_{3-6}$cycloalkyl, $C_{3-6}$cycloalkenyl, aryl, aryl$C_{1-10}$alkyl, heteroaryl, heteroaryl$C_{1-10}$ alkyl, reduced heteroaryl or reduced heteroaryl, $C_{1-10}$alkyl and $R^{8a}$, $R^{9a}$, $R^{10a}$ and $R^{11a}$ are each independently hydrogen, halo, hydroxy, amino, nitro, cyano, thiol, $C_{1-10}$alkyl, $C_{1-10}$alkoxy, $C_{1-10}$cycloalkyl, $C_{1-10}$cycloalkoxy, C(O)$R^{15}$, C(O)NR$^{15}R^6$, S(O)$R^{15}$ or halo $C_{1-10}$alkyl;
where $R^{15}$ and $R^{16}$ each independently represent hydrogen or $C_{1-10}$alkyl.

In compounds of formula (IIa):
When $R^{1a}$ represents a group defined in (i) this is preferably a $C_{10-25}$ e.g. a $C_{10-20}$ branched or unbranched alkyl group, advantageously a $C_{12-18}$ e.g. a $C_{14-18}$ branched or unbranched alkyl group, optionally interrupted by one or more oxygen atoms. Optional substituents for said alkyl groups are preferably selected from one or more of aryl e.g. phenyl; heteroaryl e.g. thienyl; aryloxy, e.g. phenoxy; heteroaryloxy, e.g. benzoxazinyloxy; —$CO_2R^{13}$ e.g. COOH; $NR^{13}R^{14}$ e.g. $NH_2$; —$CONR^{13}R^{14}$ e.g. $CONHCH_3$; cyano, nitro, halogen and OH. $R^{13}$ and $R^{14}$ preferably each independently represent hydrogen or $C_{1-6}$alkyl.

When $R^{1a}$ represents a group defined by (ii) this is preferably a $C_{10-25}$ e.g. a $C_{10-20}$ branched or unbranched alkenyl or alkynyl group, advantageously a $C_{14-18}$ branched or unbranched alkenyl or alkynyl group. Preferred optional substituents are those defined as preferred substituents in group (i).

When $R^{1a}$ represents a group defined by (iii) the $C_{1-9}$ group preferably contains one or two oxygen atoms. Preferred optional substituents are as defined above for groups (i) and (ii).

When $R^{1a}$ represents a group defined by (iv) preferred substituents are as defined above for groups (i)-(iii).

When $R^{1a}$ represents a group defined by (v) preferred substituents are selected from $OR^{17}$, $CO_2R^{13}$, $C(O)NR^{13}R^{14}$, $NR^4C(O)R^{13}$ and aryl $C_{1-10}$alkyl. The phenyl group $R^{1a}$ and any additional phenyl group or moiety in the substituent may also be substituted by one or more of halogen, alkyl or haloalkyl.

When $R^{1a}$ represents a group defined by (vi) this is preferably selected from naphthyl, pyridyl, pyrrolyl and piperidinyl.

$R^{1a}$ is preferably selected from groups (i) and (v) defined above.

$R^{1a}$ is preferably $C_{10-20}$ branched or unbranched alkyl, optionally interrupted by one or two oxygen atoms and/or optionally substituted by one or more of aryl, eg. phenyl; aryloxy e.g. phenoxy wherein the phenyl moiety may be optionally substituted by alkyl, haloalkyl, halogen or phenoxy; heteroaryl, eg. thienyl; heteroaryloxy e.g. benzoxazinyloxy (which may optionally carry an oxo substituent); cyano, nitro, —$CO_2R^{13}$, —$NR^{13}R^{14}$, —$CONR^{13}R^{14}$, OH and halogen.

$R^{1a}$ is also advantageously phenyl substituted by one or more, but most preferably one, of $OR^{17}$, —$CO_2R^{13}$, —$C(O)NR^{13}R^{14}$, $NR^{14}C(O)R^{13}$ and aryl $C_{1-10}$alkyl.

$R^{13}$ and $R^{14}$ preferably each independently represent hydrogen or $C_{1-6}$alkyl.

$R^{17}$ preferably represents phenyl, optionally substituted by alkyl, haloalkyl, halogen or phenoxy, wherein the phenyl moiety may also be optionally substituted by alkyl, haloalkyl or halogen.

Most preferably $R^{1a}$ is an unbranched alkyl chain having 14, 15, 16, 17 or 18 carbon atoms.

$R^{8a}$ is preferably hydrogen or halogen eg. fluorine; most preferably hydrogen.

$R^{9a}$ is preferably hydrogen or lower branched or unbranched alkyl having 1 to 10 carbon atoms, preferably 1 to 6 carbon atoms, preferably methyl, cyclic alkyl having 3 to 6 carbon atoms, preferably cyclopropyl, halo$C_{1-6}$alkyl, preferably trifluoromethyl or a halogen, preferably chlorine or fluorine;

$R^{10a}$ is preferably hydrogen, lower branched or unbranched alkyl having 1 to 10 carbon atoms, preferably 1-6 carbon atoms preferably methyl, cyclic alkyl having 3 to 6 carbon atoms preferably cyclopropyl, halo$C_{1-6}$alkyl preferably trifluoromethyl or a halogen preferably chlorine or fluorine;

$R^{11a}$ is preferably hydrogen, halogen, eg. fluorine; or branched or unbranched alkyl having 1 to 10 carbon atoms, preferably 1-6 carbon atoms, eg. methyl.

Preferably, in compounds of formula (IIa) at least one of $R^{8a}$, $R^{9a}$, $R^{10a}$ and $R^{11a}$ represents a substituent other than hydrogen. Thus, for example, $R^{8a}$ may represent a hydrogen atom and $R^{9a}$, $R^{10a}$ and $R^{11a}$ are as defined above. In a further preferred embodiment each of $R^{8a}$ and $R^{11a}$ represents a hydrogen atom, $R^{9a}$ represents a substituent as defined above and $R^{10a}$ represents a hydrogen atom or a substituent. In a further embodiment $R^{8a}$, $R^{9a}$ and $R^{10a}$ represent hydrogen and $R^{10a}$ represents a substituent as defined above, eg. methyl. Most preferably each of $R^{8a}$, $R^{10a}$ and $R^{11a}$ represents a hydrogen atom, and $R^{9a}$ represents a substituent as defined above, advantageously a $C_{1-6}$alkyl group, especially methyl.

A further group of novel compounds within the scope of formula (II) is that wherein $R^1$ is as defined for formula (II) and at least one of $R^8$, $R^9$, $R^{10}$ and $R^1$ represents a $C_{8-20}$ alkyl group, preferably a $C_{8-10}$ alkyl group. Most preferably in this embodiment either $R^9$ or $R^{10}$ represents a $C_{8-10}$ alkyl group and the remaining substituents on the benzene ring are all hydrogen.

Examples of pharmaceutically acceptable salts of the above compounds include those derived from organic acids such as methanesulphonic acid, benzenesulphonic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl) aminomethane; and the like.

Salts may be prepared in a conventional manner using methods well known in the art. Acid addition salts of said basic compounds may be prepared by dissolving the free base compounds according to the first or second aspects of the invention in aqueous or aqueous alcohol solution or other suitable solvents containing the required acid. Where a compound of formula (I) contains an acidic function a base salt of said compound may be prepared by reacting said compound with a suitable base. The acid or base salt may separate directly or can be obtained by concentrating the solution eg. by evaporation. The compounds of this invention may also exist in solvated or hydrated forms.

The invention also extends to prodrugs of the aforementioned compounds. A prodrug is commonly described as an inactive or protected derivative of an active ingredient or a drug which is converted to the active ingredient or drug in the body.

Representative compounds according to the first and/or second aspects of the invention are those which include:

TABLE I

| Reference Number | Structure | Compound Name |
|---|---|---|
| 1 | 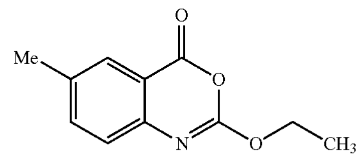 | 2-Ethoxy-6-methyl-4H-3,1-benzoxazin-4-one |
| 2 | 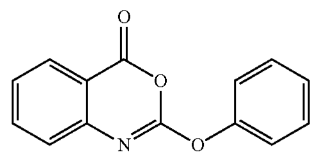 | 2-Phenoxy-4H-3,1-benzoxazin-4-one |
| 3 | 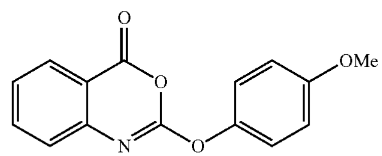 | 2-(4-Methoxyphenoxy)-4H-3,1-benzoxazin-4-one |
| 4 | 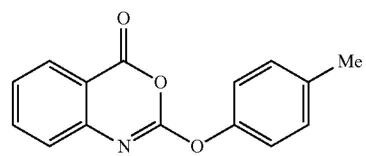 | 2-(4-Methylphenoxy)-4H-3,1-benzoxazin-4-one |
| 5 | 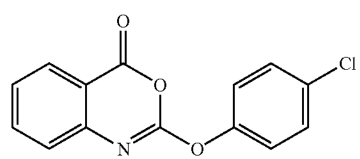 | 2-(4-Chlorophenoxy)-4H-3,1-benzoxazin-4-one |
| 6 | 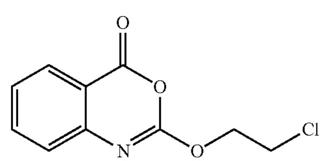 | 2-(2-Chloroethoxy)-4H-3,1-benzoxazin-4-one |

TABLE I-continued

| Reference Number | Structure | Compound Name |
|---|---|---|
| 7 | 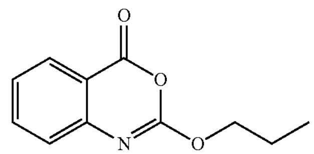 | 2-Propoxy-4H-3,1-benzoxazin-4-one |
| 8 | 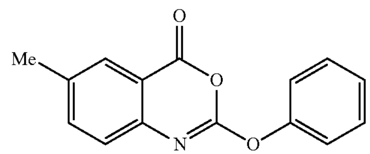 | 6-Methyl-2-phenoxy-4H-3,1-benzoxazin-4-one |
| 9 | 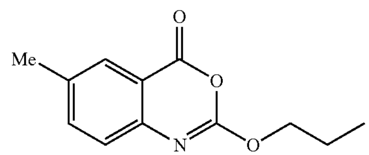 | 6-Methyl-2-propoxy-4H-3,1-benzoxazin-4-one |
| 10 | 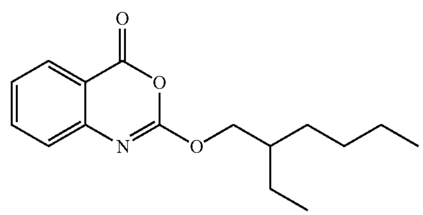 | 2-(2-Ethylhexyloxy)-4H-3,1-benzoxazin-4-one |
| 11 | 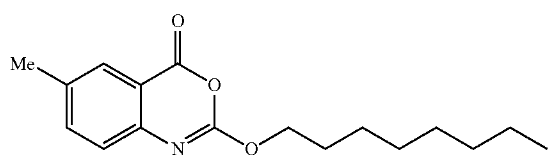 | 6-Methyl-2-octyloxy-4H-3,1-benzoxazin-4-one |
| 12 | 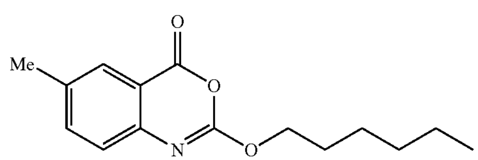 | 2-Hexyloxy-6-methyl-4H-3,1-benzoxazin-4-one |

TABLE I-continued

| Reference Number | Structure | Compound Name |
|---|---|---|
| 13 | 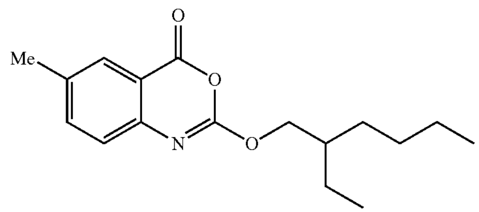 | 2(2-Ethylhexyloxy)-6-methyl-4H-3,1-benzoxazin-4-one |
| 14 | 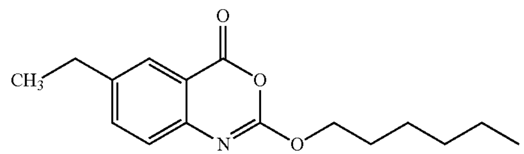 | 6-Ethyl-2-hexyloxy-4H-3,1-benzoxazin-4-one |
| 15 | 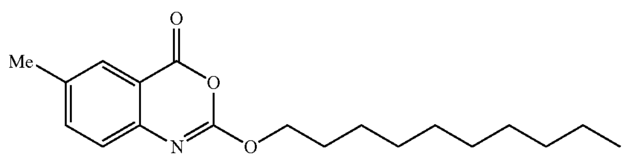 | 2-Decyloxy-6-methyl-4H-3,1-benzoxazin-4-one |
| 16 | 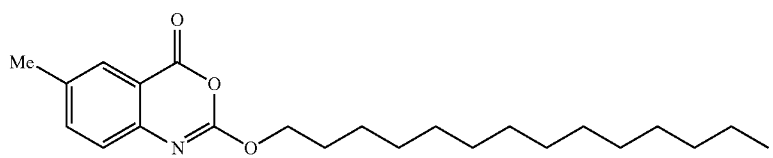 | 6-Methyl-2-tetradecyloxy-4H-3,1-benzoxazin-4-one |
| 17 | 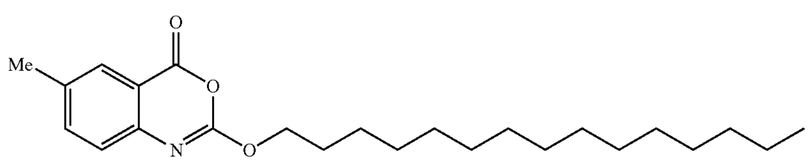 | 6-Methyl-2-pentadecyloxy-4H-3,1-benzoxazin-4-one |

TABLE I-continued
| Reference Number | Structure | Compound Name |
|---|---|---|
| 18 | 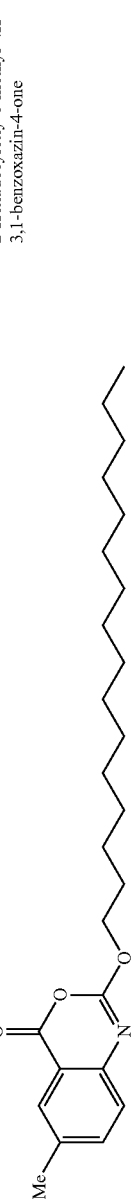 | 2-Hexadecyloxy-6-methyl-4H-3,1-benzoxazin-4-one |
| 19 | 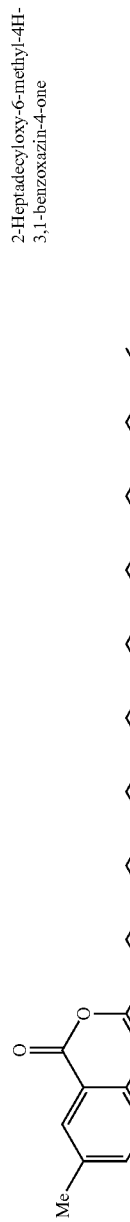 | 2-Heptadecyloxy-6-methyl-4H-3,1-benzoxazin-4-one |
| 20 | 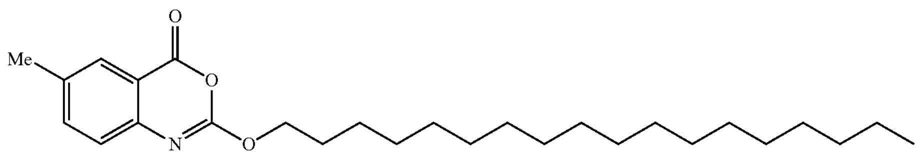 | 6-Methyl-2-octadecyloxy-4H-3,1-benzoxazin-4-one |
| 21 | 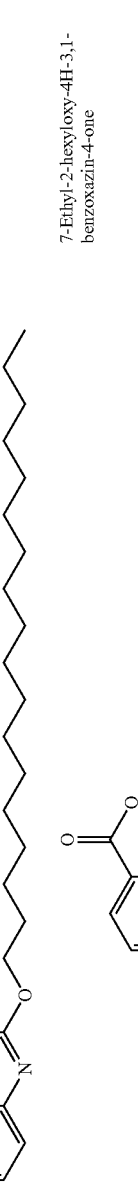 | 7-Ethyl-2-hexyloxy-4H-3,1-benzoxazin-4-one |
| 22 | 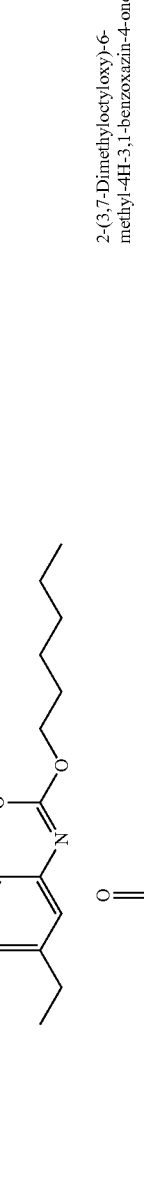 | 2-(3,7-Dimethyloctyloxy)-6-methyl-4H-3,1-benzoxazin-4-one |
| 23 | 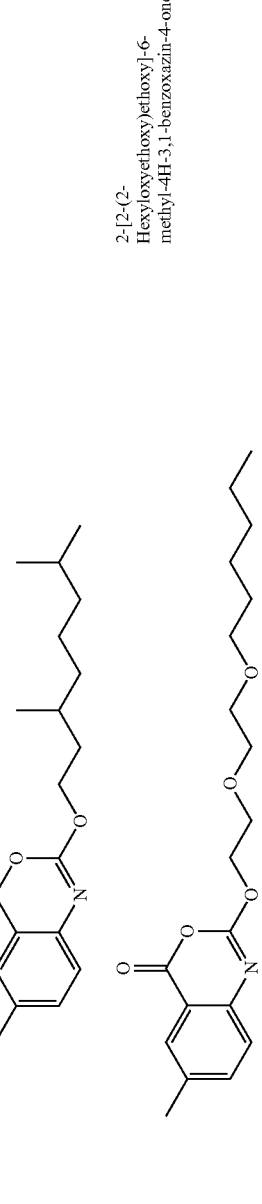 | 2-[2-(2-Hexyloxyethoxy)ethoxy]-6-methyl-4H-3,1-benzoxazin-4-one |

TABLE I-continued

| Reference Number | Structure | Compound Name |
|---|---|---|
| 24 | 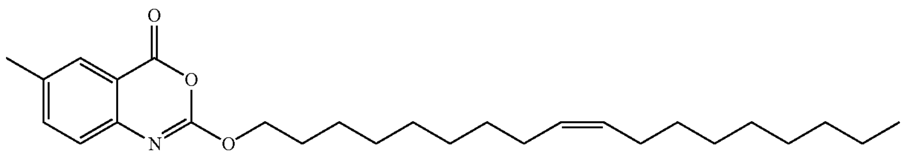 | (Z)-6-Methyl-2-(octadeca-9-enyloxy)-4H-3,1-benzoxazin-4-one |
| 25 | 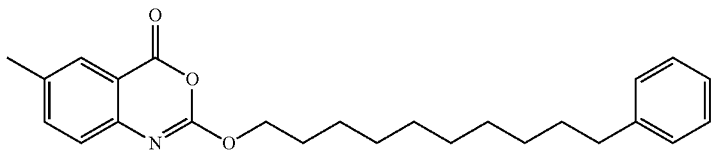 | 6-Methyl-2-(10-phenyldecyloxy)-4H-3,1-benzoxazin-4-one |
| 26 | 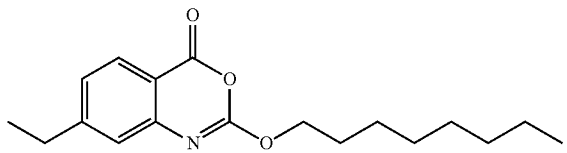 | 7-Ethyl-2-octyloxy-4H-3,1-benzoxazin-4-one |
| 27 | 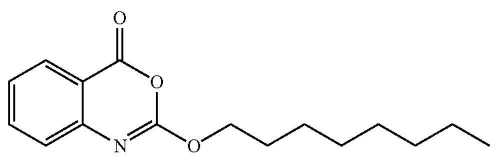 | 2-Octyloxy-4H-3,1-benzoxazin-4-one |
| 28 | 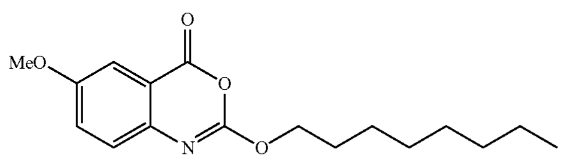 | 6-Methoxy-2-octyloxy-4H-3,1-benzoxazin-4-one |
| 29 | 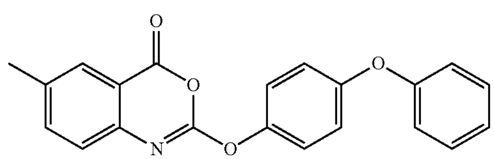 | 6-Methyl-2-(4-phenoxyphenoxy)-4H-3,1-benzoxazin-4-one |

TABLE I-continued

| Reference Number | Structure | Compound Name |
|---|---|---|
| 30 | 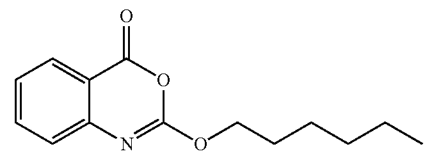 | 2-Hexyloxy-4H-3,1-benzoxazin-4-one |
| 31 | 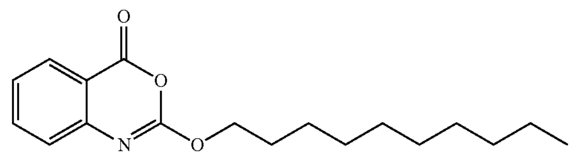 | 2-Dodecyloxy-6-methyl-4H-3,1-benzoxazin-4-one |
| 32 | 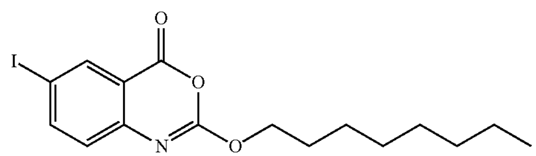 | 6-Iodo-2-octyloxy-4H-3,1-benzoxazin-4-one |
| 33 | 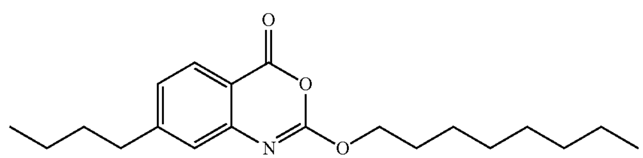 | 7-Butyl-2-Octyloxy-4H-3,1-benzoxazin-4-one |
| 34 | 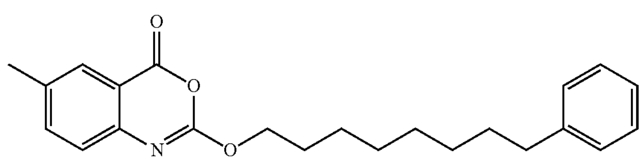 | 6-Methyl-2-(8-phenyloctyloxy)-4H-3,1-benzoxazin-4-one |
| 35 | 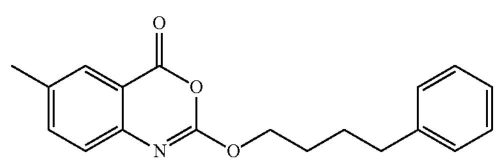 | 6-Methyl-2-(4-phenylbutyloxy)-4H-3,1-benzoxazin-4-one |

TABLE I-continued

| Reference Number | Structure | Compound Name |
|---|---|---|
| 36 | 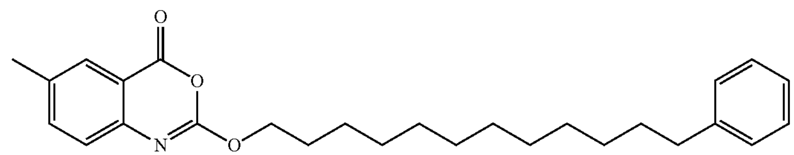 | 6-Methyl-2-(12-phenyldodecyloxy)-4H-3,1-benzoxazin-4-one |
| 37 | 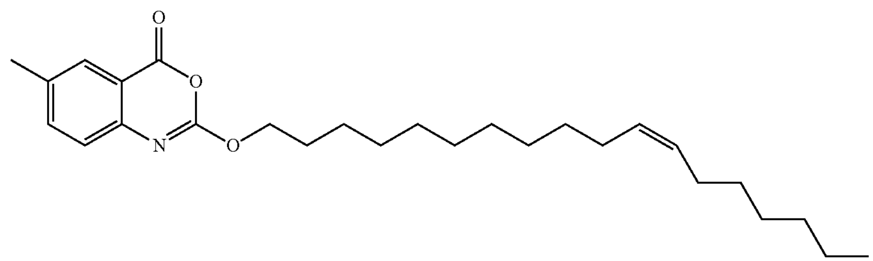 | (Z)-6-Methyl-2-(octadeca-11-enyloxy)-4H-3,1-benzoxazin-4-one |
| 38 | 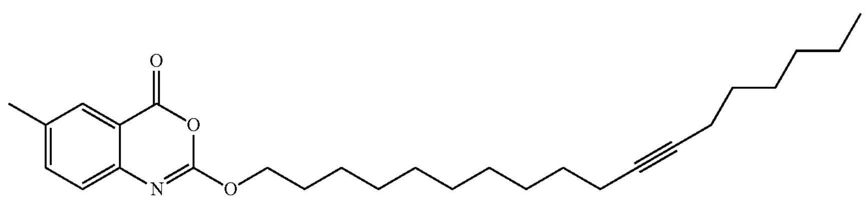 | 6-Methyl-2-(octadeca-11-ynyloxy)-4H-3,1-benzoxazin-4-one |
| 39 | 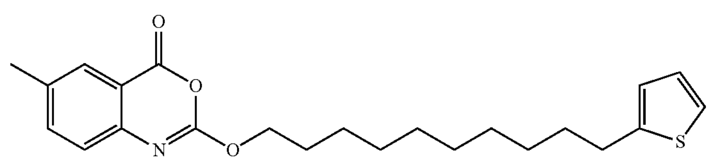 | 6-Methyl-2-[-10-(thien-2-yl)-decyloxy]-4H-3,1-benzoxazin-4-one |
| 40 | 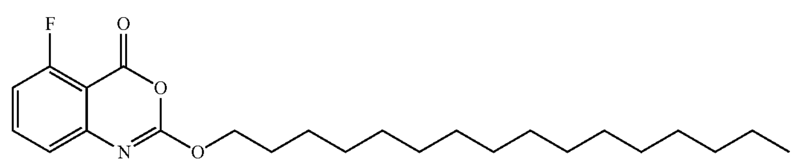 | 5-Fluoro-2-hexadecyloxy-4H-3,1-benzoxazin-4-one |

TABLE 1-continued

| Reference Number | Structure | Compound Name |
|---|---|---|
| 41 | 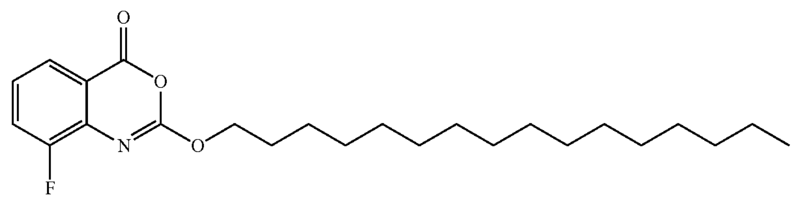 | 8-Fluoro-2-hexadecyloxy-4H-3,1-benzoxazin-4-one |
| 42 | 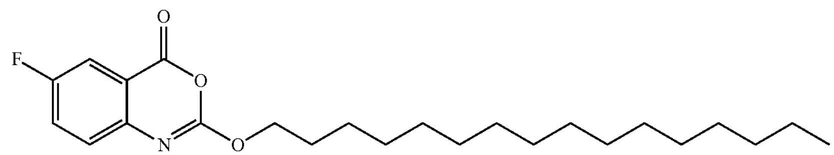 | 6-Fluoro-2-hexadecyloxy-4H-3,1-benzoxazin-4-one |
| 43 | 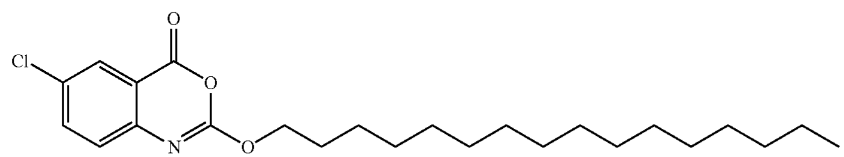 | 6-Chloro-2-hexadecyloxy-4H-3,1-benzoxazin-4-one |
| 44 | 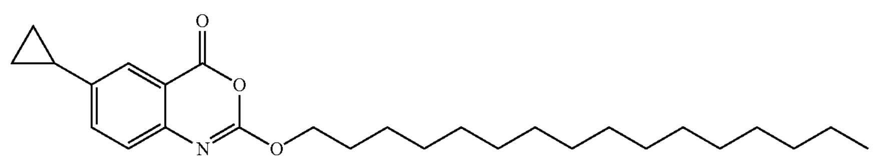 | 6-Cyclopropyl-2-hexadecyloxy-4H-3,1-benzoxazin-4-one |
| 45 | 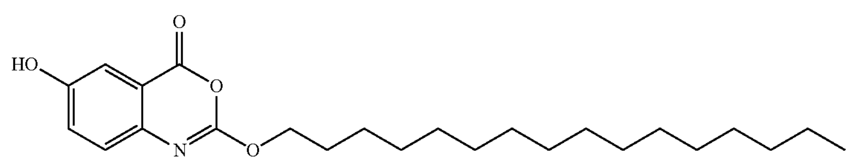 | 2-Hexadecyloxy-6-hydroxy-4H-3,1-benzoxazin-4-one |
| 46 | 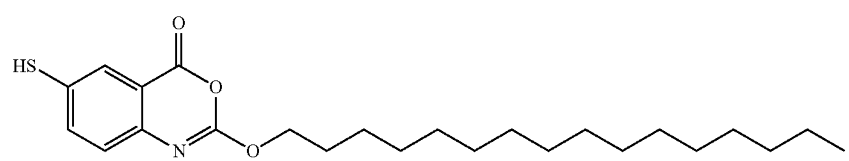 | 2-Hexadecyloxy-6-mercapto-4H-3,1-benzoxazin-4-one |

TABLE I-continued

| Reference Number | Structure | Compound Name |
|---|---|---|
| 47 | 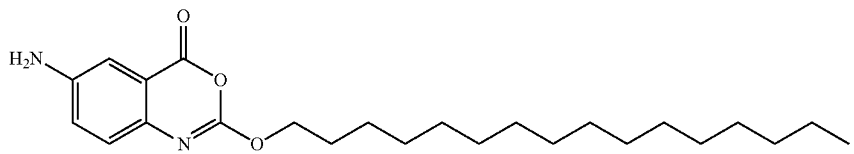 | 6-Amino-2-hexadecyloxy-4H-3,1-benzoxazin-4-one |
| 48 | 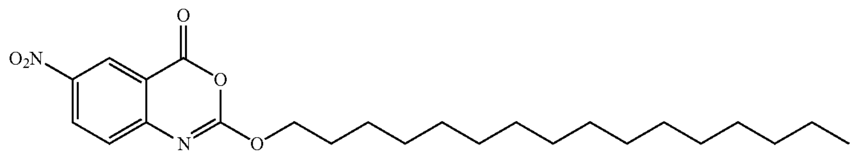 | 2-Hexadecyloxy-6-nitro-4H-3,1-benzoxazin-4-one |
| 49 | 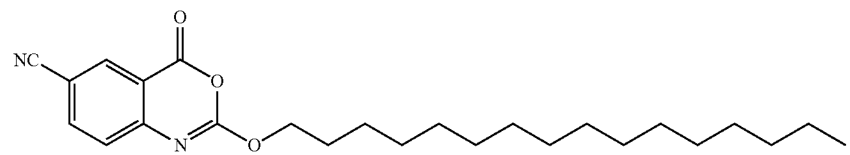 | 6-Cyano-2-hexadecyloxy-4H-3,1-benzoxazin-4-one |
| 50 | 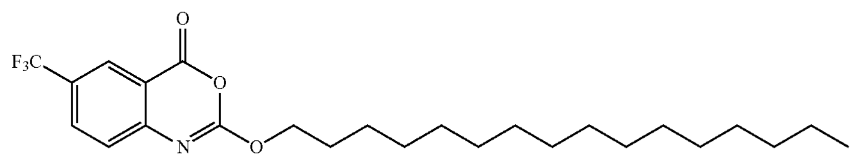 | 2-Hexadecyloxy-6-trifluoromethyl-4H-3,1-benzoxazin-4-one |
| 51 | 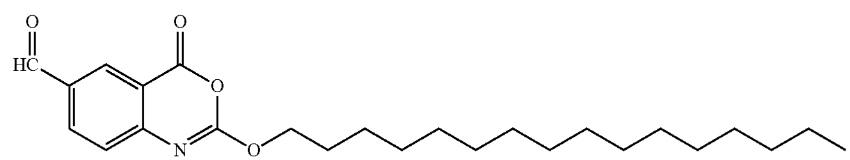 | 6-Formyl-2-hexadecyloxy-4H-3,1-benzoxazin-4-one |
| 52 | 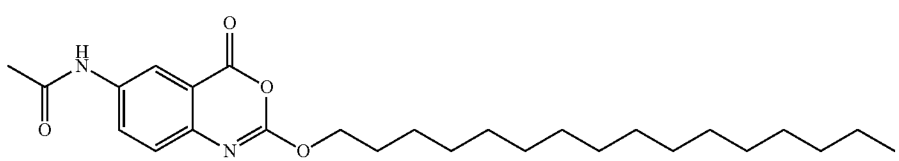 | 6-Acetamido-2-hexadecyloxy-4H-3,1-benzoxazin-4-one |

TABLE I-continued

| Reference Number | Structure | Compound Name |
|---|---|---|
| 53 | 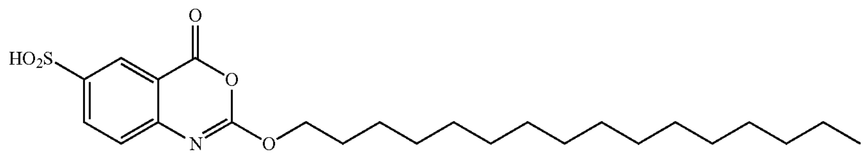 | 2-Hexadecyloxy-6-sulfo-4H-3,1-benzoxazin-4-one |
| 54 | 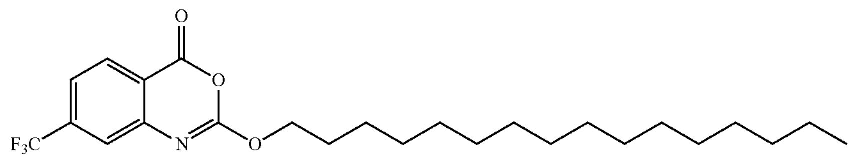 | 2-Hexadecyloxy-7-trifluoromethyl-4H-3,1-benzoxazin-4-one |
| 55 | 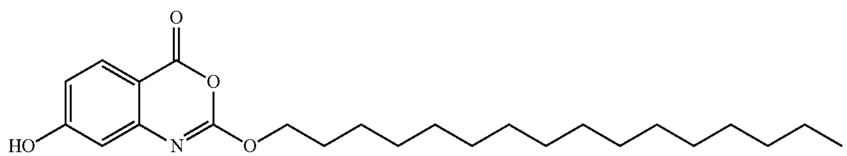 | 2-Hexadecyloxy-7-hydroxy-4H-3,1-benzoxazin-4-one |
| 56 | 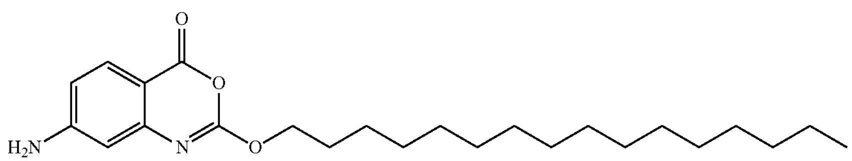 | 7-Amino-2-hexadecyloxy-4H-3,1-benzoxazin-4-one |
| 57 | 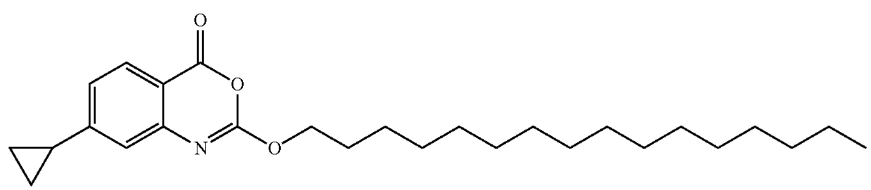 | 7-Cyclopropyl-2-hexadecyloxy-4H-3,1-benzoxazin-4-one |
| 58 | 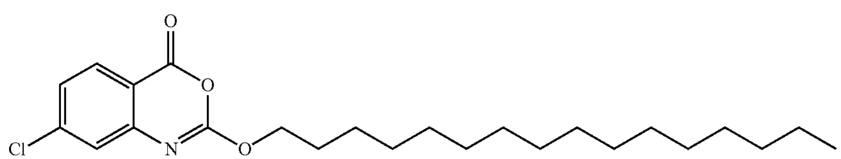 | 7-Chloro-2-hexadecyloxy-4H-3,1-benzoxazin-4-one |

TABLE I-continued

| Reference Number | Structure | Compound Name |
|---|---|---|
| 59 | 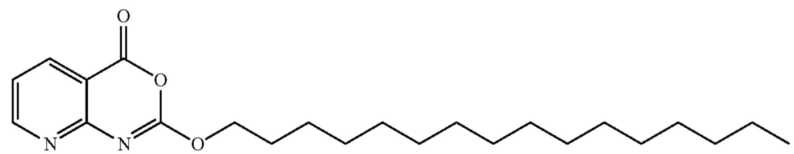 | 2-Hexadecyloxy-4H-pyrido[2,3-d][1,3]oxazin-4-one |
| 60 | 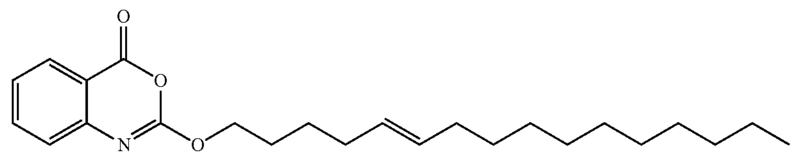 | (E)-2-(Hexadeca-5-enyloxy)-4H-3,1-benzoxazin-4-one |
| 62 | 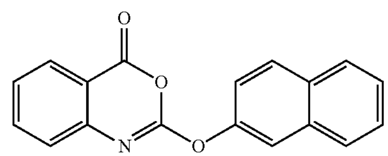 | 2-(2-Naphthyloxy)-4H-3,1-benzoxazin-4-one |
| 64 | 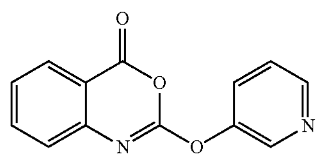 | 2-(3-Pyridyloxy)-4H-3,1-benzoxazin-4-one |
| 65 | 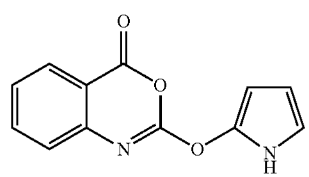 | 2-(2-Pyrrolyloxy)-4H-3,1-benzoxazin-4-one |
| 66 | 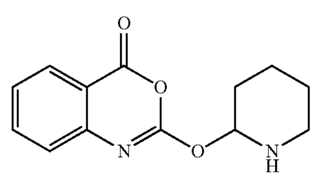 | 2-(2-Piperidinyloxy)-4H-3,1-benzoxazin-4-one |

TABLE I-continued

| Reference Number | Structure | Compound Name |
|---|---|---|
| 67 | 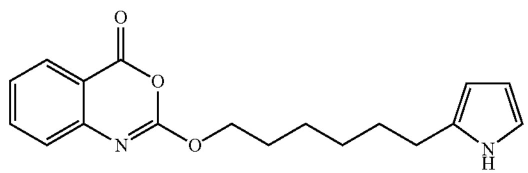 | 2-[6-(2-Pyrrolyl)hexyloxy]-4H-3,1-benzoxazin-4-one |
| 69 | 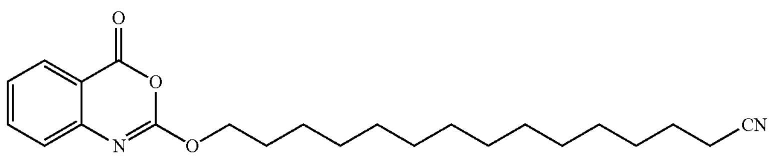 | 2-(14-Cyanotetradecyloxy)-4H-3,1-benzoxazin-4-one |
| 70 | 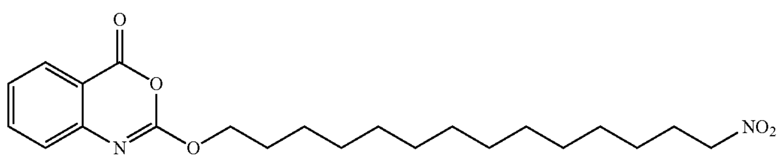 | 2-(14-Nitrotetradecyloxy)-4H-3,1-benzoxazin-4-one |
| 71 | 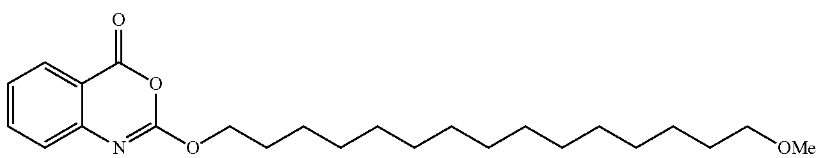 | 2-(15-Methoxypentadecyloxy)-4H-3,1-benzoxazin-4-one |
| 72 | 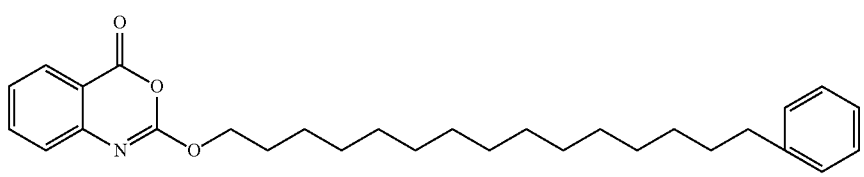 | 2-(15-Phenylpentadecyloxy)-4H-3,1-benzoxazin-4-one |
| 73 | 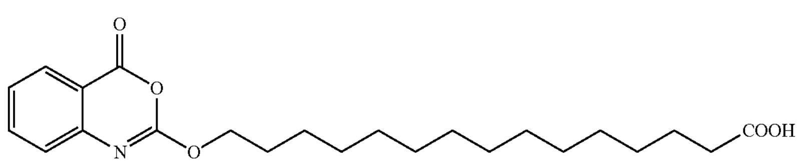 | 2-(14-Carboxytetradecyloxy)-4H-3,1-benzoxazin-4-one |

TABLE I-continued

| Reference Number | Structure | Compound Name |
|---|---|---|
| 74 | (benzoxazinone with O-(CH2)14-NH2 chain) | 2-(14-Aminotetradecyloxy)-4H-3,1-benzoxazin-4-one |
| 75 | (benzoxazinone with O-(CH2)14-OH chain) | 2-(14-Hydroxytetradecyloxy)-4H-3,1-benzoxazin-4-one |
| 76 | (benzoxazinone with O-(CH2)12-CONHMe chain) | 2-(12-N-Methylcarbamoyl dodecyloxy)-4H-3,1-benzoxazin-4-one |
| 77 | (6,7-dimethyl benzoxazinone with O-hexadecyl chain) | 2-Hexadecyloxy-6,7-dimethyl-4H-3,1-benzoxazin-4-one |

TABLE I-continued

| Reference Number | Structure | Compound Name |
|---|---|---|
| 78 | 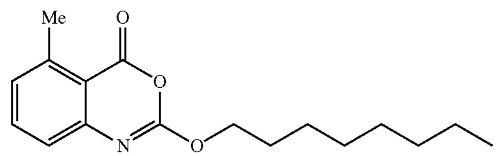 | 5-Methyl-2-octyloxy-4H-3,1-benzoxazin-4-one |
| 79 | 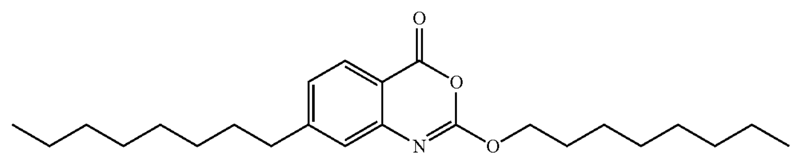 | 7-Octyl-2-octyloxy-4H-3,1-benzoxazin-4-one |
| 80 | 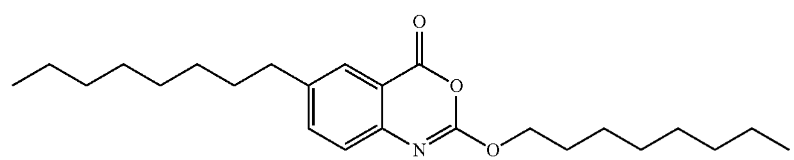 | 6-Octyl-2-octyloxy-4H-3,1-benzoxazin-4-one |
| 81 | 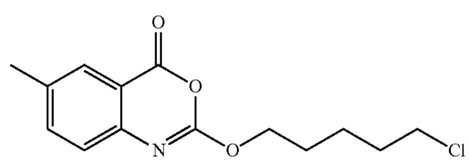 | 2-(5-Chloropentyloxy)-6-methyl-4H-3,1-benzoxazin-4-one |

TABLE I-continued

| Reference Number | Structure | Compound Name |
|---|---|---|
| 82 | 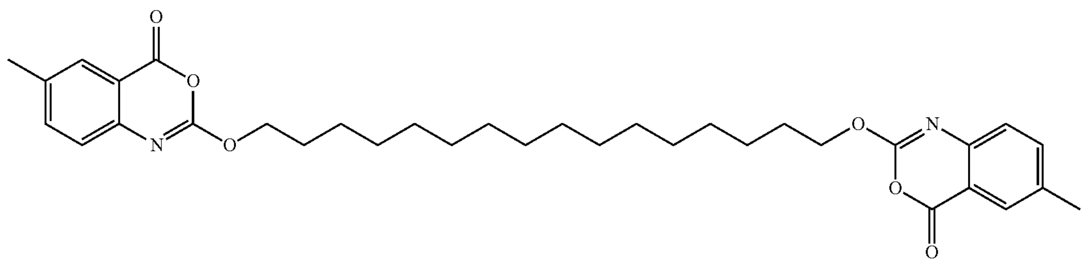 | 2,2'-(1,16-Hexadecylidenedioxy)-bis-4H-3,1-benzoxazin-4-one |
| 83 | 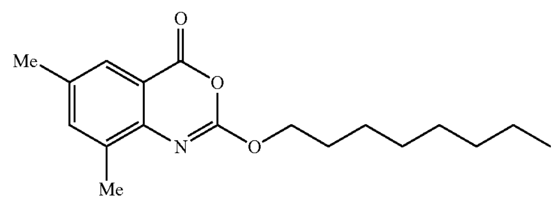 | 6,8-Dimethyl-2-octyloxy-4H-3,1-benzoxazin-4-one |
| 84 | 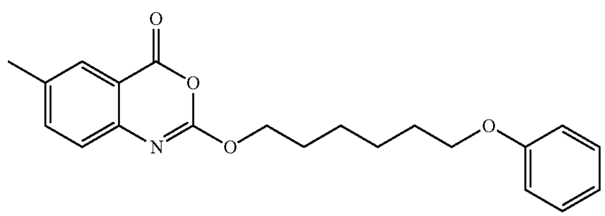 | 6-Methyl-2-(6-phenoxyhexyloxy)-4H-3,1-benzoxazin-4-one |
| 85 | 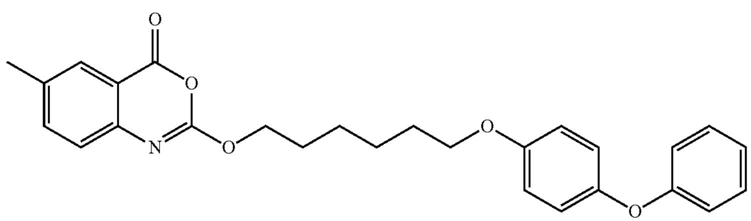 | 6-Methyl-2-[6-(4-phenoxyphenoxy)hexyloxy]-4H-3,1-benzoxazin-4-one |

Apart from compounds 1-3, 6, 7 and 9, the compounds of Table 1 are believed to be novel and as such form preferred embodiments of the present invention.

Preferred compounds of formula (II) listed in Table 1 include compounds numbers 4, 5, 8, 10, 11, 12, 13, 14, 21, 26, 27, 28, 30, 32, 33, 34, 35 and 78.

These specific compounds are believed to be novel and as such form a further aspect of the invention.

Preferred compounds of formula (IIa) listed in Table 1 include compounds numbers 15, 16, 17, 18, 19, 20, 22, 23, 24, 25, 29, 31, 36, 37, 38, 39, 79, 80, 81, 82, 84 and 85.

Particularly preferred compounds of formula (IIa) are:
15: 2-Decyloxy-6-methyl-4H-3,1-benzoxazin-4-one
16: 6-Methyl-2-tetradecyloxy-4H-3,1-benzoxazin-4-one
18: 2-Hexadecyloxy-6-methyl-4H-3,1-benzoxazin-4-one Preferred compounds of the invention listed above extend to the tautomers thereof, as well as (but not limited to) pharmaceutically acceptable salts, esters, amides or prodrugs thereof or a derivative optionally with one or more lipid groups (natural or synthetic) attached.

A third aspect of the invention provides a process for the manufacture of any one or more of the novel compounds or derivatives according to the first or second aspects of the invention. Thus, the present invention provides a process for the preparation of a novel compound of formula (II) in particular a compound of formula (IIa) which process comprises:

Process (A) reacting a compound of formula (IV):

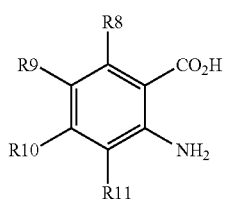

(IV)

with a compound of formula (V):

(V)

or:

Process (B) cyclising a compound of formula (VI)

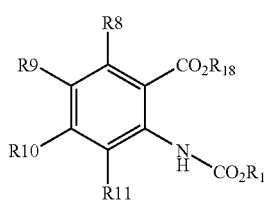

(VI)

wherein $R^1$ and $R^8$-$R^{11}$ are as hereinbefore defined and $R^{18}$ is hydrogen or $C_{1-6}$alkyl.

or:

Process (C) reacting a compound of formula (VII)

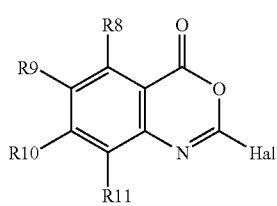

(VII)

with a compound of formula (VIII):

$$R^1OH \qquad (VIII)$$

or:

Process (D) converting a compound of formula (I), (II) or (IIa) into a different compound of formula (IIa), by, for example, (i) reduction of a compound of formula (IIa) wherein any of $R^1$, $R^8$, $R^9$, $R^{10}$ and $R^{11}$ contains an alkenyl or alkynyl group or moiety, to the corresponding alkyl or alkenyl group or moiety; or (ii) alkylation of a compound of formula (IIa) where one or more of $R^8$, $R^9$, $R^{10}$ and $R^{11}$ represents a halogen atom.

Process (A) may be effected by reacting a compound of formula (IV) with a chloroformate of formula (V). The process is preferably carried out under basic conditions, e.g. using pyridine. The reaction may be cooled to avoid overheating. The resulting carbamate intermediate is then cyclised by reaction with excess chloroformate or by addition of another cyclisation reagent, which promotes ring closure. Suitable cyclisation reagents include for example, methyl chloroformate, carbonyl diimidazole, acetic anhydride, phosgene, oxalyl chloride, thionyl chloride or a peptide coupling agent such as dicyclohexyl carbodiimide (DCC). The cyclisation reagent is preferably phosgene, triphosgene or thionyl chloride. It will be understood by those skilled in the art that when a chloroformate is used to effect the cyclisation, this may be provided by employing an excess of the compound of formula (V). Preferably, however, a low molecular weight chloroformate is employed, on grounds of cost and ease of removing the resulting alcohol.

Compounds of formula (V) for use in the process (A) may be prepared by standard methods well known in the art, e.g. by reaction of the corresponding alcohol $R^1OH$ with phosgene in a solvent such as toluene. The product may be isolated in conventional manner by removal of solvent and volatile by-products.

Process (B) may be effected by reaction of a compound (VI) wherein $R^{18}$ is hydrogen, in the presence of a cyclisation reagent, e.g. an alkyl chloroformate, for example as described for process (A). Alternatively a compound (VI) may be cyclised by treatment with a dehydrating agent such as concentrated sulphuric acid.

Compounds (VI) wherein $R^{18}$ is an alkyl group may be prepared by reacting an ester corresponding to formula (IV) with e.g. phosgene and a base such as pyridine to afford the corresponding isocyanate, followed by treatment with an alcohol $R^1OH$. If desired the ester (i.e. where $R^{18}$ is alkyl) may be hydrolysed to the corresponding acid ($R^{18}$=H) using for example lithium hydroxide in e.g. aqueous tetrahydrofuran or aqueous dioxane.

It will be appreciated that process (A) also proceeds via an intermediate of formula (VI) and is hence a variant of process (B).

Process (C) may be effected by reacting a compound of formula (VII) with an alcohol $R^1OH$ in the presence of a base, e.g. Hunig's base (diisopropylethylamine). A compound of formula (VII) may be prepared from the corresponding anhydride of formula (IX)

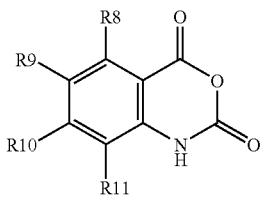

(IX)

by reaction with for example phosphorus oxychloride (POCl$_3$) at elevated temperature e.g. 100° C.

The anhydride of formula (IX) may itself be obtained by cyclisation of a compound of formula (IV), for example using phosgene or a synthetic equivalent.

In process (D), reduction of an alkenyl or alkynyl group may be effected for example by catalytic hydrogenation using e.g. 10% palladium on charcoal in an alcoholic solvent, such as ethanol, under 1 atmosphere of hydrogen gas.

Alkylation according to process (D)(ii) may be effected using a Stille or other palladium catalysed cross-coupling process, using e.g. tetra-alkyl tin such as tetramethyl tin and PhCH$_2$Pd(PPh$_3$)$_2$Cl in HMPA at elevated temperature e.g. 50-100° C. Other halides or pseudohalides e.g. triflates may be employed as starting materials.

A fourth aspect of the invention is a compound according to the first and second aspects of the invention (i.e. compounds of formulae (I), (II) and (IIa)), for use in medicine. Preferred features of the first and second aspects of the invention also apply to the fourth aspect. Further details of the fourth aspect of the invention are set out in the text which follows.

A fifth aspect of the invention relates to a compound according to the first and/or second aspects of the invention for use in the inhibition of an enzyme whose preferred mode of action is to catalyse the hydrolysis of an ester functionality. This includes both in vivo and in vitro uses and other uses such as industrial uses. Such an enzyme is one which catalyses the breakdown of a substrate containing an ester functionality by the addition of water, resulting in the cleavage of a chemical bond. Such enzymes are involved in key processes in the body. Enzymes according to this invention include lipases (hydrolyse fatty acid esters), esterases (hydrolyse esters) and phosphatases (hydrolyse phosphate esters).

The enzyme is preferably a lipase. Lipases include pancreatic lipase, gastric lipase, lipoprotein lipase, lingual lipase, adipose tissue lipase, hormone sensitive lipase, phospholipase A1, A2, B, C, D etc., hepatic lipase, and other triacyl, diacyl and monoacylglycerol lipases in the mammalian body. Many similar such lipases are also known in plants, fungi and microorganisms.

Also covered are esterase enzymes and phosphatase enzymes. Esterase enzymes include pig liver esterase, cholesteryl esterase, retinyl esterase, 1-alkyl-2-acetylglycerophosphocholine esterase, carboxylic ester hydrolases, and cholesterol esterase. Phosphatase enzymes include serine/threonine phosphatases PP 1, PP2 and PP3, phosphoprotein phosphatase, myosin-light-chain phosphatase, protein phosphoprotein 2C, and protein tyrosine phosphatase.

Compounds according to the invention, for use in medicine, are primarily for use in relation to the prevention and/or treatment of a medical condition such as obesity, hyperlipaemia, hyperlipidaemia and related diseases such as hyperglycaemia (type II diabetes), hypertension, cardiovascular disease, stroke, gastrointestinal disease and gastrointestinal conditions. Compounds according to the first and second aspect of the invention are useful in these and other conditions due to their ability to inhibit an enzyme whose preferred mode of action is to catalyse the hydrolysis of an ester functionality (in vivo, as the enzyme naturally occurs). The invention also relates to non-medical weight loss, such as cosmetic weight loss and includes improving bodily appearance in general. Throughout this text, the prevention and/or treatment of any disorder means any effect which mitigates any damage or any medical disorder, to any extent, and includes prevention and treatment themselves. The term "treatment" means any amelioration of disorder, disease, syndrome, condition, pain or a combination of two or more thereof.

Clearly, an important application of the invention is in relation to weight loss (of all kinds as described above) in humans. However, the invention applies to medical and non-medical weight loss in any animal whose metabolism of fat and fat derivatives involves an enzyme whose preferred mode of action is to catalyse the hydrolysis of an ester functionality (in vivo, as the enzyme naturally occurs). Thus, the invention has veterinary application and is particularly useful in relation to medical and non-medical weight loss in companion animals such as pet cats and dogs as well as in animals which provide meat for human consumption. In the case of the latter, the application of the present invention is to reduce fat content in order to provide a leaner meat product.

It is also believed that the compounds may be useful in reducing levels of toxins (e.g. dioxins and PCBs) stored in body fat. Without wishing to be bound by theory, it is believed that increasing the amount of undigested fat passing through the body enhances diffusion of toxins from fat stored in the body into fats in the blood, and thence into the intestine.

The fifth aspect of the invention has important applications. It includes test and diagnostic methods and the control and inhibition of unwanted enzymes, preferably lipases, in any process or in any product. The processes or products, which preferably involve a lipase, include: processing of agricultural commodities (e.g. oilseeds), recovery and isolation of enzymes from biotechnological processes (e.g. involving lysis of microorganisms), the manufacture and extraction of crude oil (especially oil and plastics), the industrial manufacture of triglycerides or other fats, manufacture of healthcare goods which comprise surfactants, soap or detergent (e.g. bath oils, creams), the manufacturing and processing of liposomes (e.g. healthcare products, diagnostics, gene therapy), the treatment of industrial waste (e.g. paper effluent treatment) and preventing the degradation of foodstuff which comprises a fat (e.g. chocolate processing). Thus, the invention also relates to these products and processes, e.g. a foodstuff which comprises a compound according to the first aspect of the invention, in particular foodstuffs which have a high fat content such as cakes, biscuits, pastry-products and the like and chocolate products. The preferred features of the fifth aspect of the invention, including an enzyme whose preferred mode of action is to catalyse the hydrolysis of an ester functionality (in vivo, as the enzyme naturally occurs) are as discussed for the previous aspects of the invention.

A sixth aspect of the invention provides a composition comprising a novel compound according to the first or second aspect of the invention, in combination with a pharmaceutically acceptable carrier or diluent. Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration).

The compounds according to the invention for use in the aforementioned indications may be administered by any convenient method, for example by oral (including by inhalation), parenteral, mucosal (e.g. buccal, sublingual, nasal), rectal or transdermal administration and the compositions adapted accordingly.

For oral administration, the compounds can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections.

Conveniently the composition is in unit dose form such as a tablet, capsule or ampoule.

The compositions of the sixth aspect of the invention are useful in the prevention and/or treatment of obesity, obesity-related disorder, other medical weight loss and non-medical related weight loss. Preferred features of this aspect of the invention are as described above for the first to fifth aspects of the invention.

A seventh aspect of the invention provides a process for the manufacture of a composition according to the sixth aspect of the invention. The manufacture can be carried out by standard techniques well known in the art and involves combining a compound according to the first or second aspect of the invention and the pharmaceutically acceptable carrier or diluent. The composition may be in any form including a tablet, a liquid, a capsule, and a powder or in the form of a food product, e.g. a functional food. In the latter case the food product itself may act as the pharmaceutically acceptable carrier.

An eighth aspect of the invention provides a method for the prevention and/or treatment of obesity or an obesity-related disorder, the method comprising the administration of a compound according to the first or second aspect of the invention, preferably in combination with a pharmaceutically acceptable carrier or diluent (as per the sixth aspect of the invention). Obesity-related disorders include hyperlipeamia, hyperlipideamia, hyperglycaemia, hypertension, cardiovascular disease, stroke, gastrointestinal disease and gastrointestinal conditions. The compound or composition is preferably administered to a patient in need thereof and in a quantity sufficient to prevent and/or treat the symptoms of the condition, disorder or disease. For all aspects of the invention, particularly medical ones, the administration of a compound or composition has a dosage regime which will ultimately be determined by the attending physician and will take into consideration such factors such as the compound being used, animal type, age, weight, severity of symptoms, method of administration, adverse reactions and/or other contraindications. Specific defined dosage ranges can be determined by standard design clinical trials with patient progress and recovery being fully monitored. Such trials may use an escalating dose design using a low percentage of the maximum tolerated dose in animals as the starting dose in man.

The physiologically acceptable compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (1) or a physiologically acceptable salt thereof calculated as the free base, the compound being administered 1 to 4 times per day. Suitably the compounds will be administered for a period of continuous therapy, for example for a week or more.

A ninth aspect of the invention provides a cosmetic method (non-therapeutic) for maintaining a given weight, or for cosmetic weight loss, the method comprising the administration of a compound according to the first or second aspect of the invention, preferably in combination with a pharmaceutically acceptable carrier or diluent (as per the sixth aspect of the invention). The compound or composition is preferably administered to a subject in need or in desideratum thereof and in a quantity sufficient to maintain a given weight or for cosmetic weight loss.

The eighth and ninth aspects of the invention relate to methods which are applicable to humans and other animals, in particular companion animals (such as dogs and cats) and other animals which provide meat for human consumption, such as cattle, pigs and sheep (all of any age).

The invention will now be described with reference to the following non-limiting examples.

Biological Test Methods and Results

Test Compounds

The benzoxazinone compounds used in the following tests are identified by the reference number assigned in Table 1 hereinbefore.

Measurement of Lipase Activity Using a Quinine Diimine Dye Calorimetric Assay

The inhibitory activity of the selected compounds to pancreatic lipase was measured in the following assay available from Sigma Ltd (Lipase-PS™, catalog number 805-A):

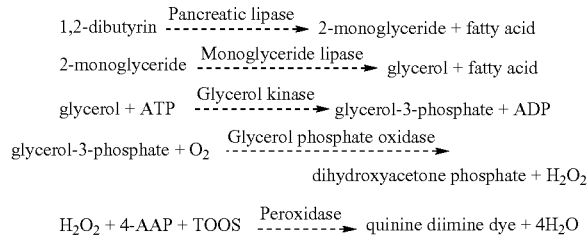

The glycerol released from the action of pancreatic and monoglyceride lipase was oxidised to release $H_2O_2$. The peroxidase reaction step then produces a quinine dye which is pink in colour and absorbs light at a wavelength of 550 nm.

Inhibitor

Individual test compounds were dissolved in DMSO (dimethyl sulphoxide) at 10 mM. DMSO was used to avoid any problems with compounds being water-insoluble. For individual compounds, the $IC_{50}$ (concentration at which lipase activity is inhibited to one half of the maximum) was calculated by measuring the inhibitory activity from log-dose response curves using a range of inhibitor concentrations.

Results

A range of compounds was assayed in the quinine diimine dye calorimetric assay which provides a rapid method to measure lipase inhibitory activity. None of the compounds tested interfered with the colorimetric reaction, i.e. they did not give false positive results.

A range of inhibitory activities for the tested benzoxazinone compounds was observed, indicating that these compounds are inhibitors of human pancreatic lipase. The following compounds had an $IC_{50}$ of $\leq 100$ nM:

Compounds 9, 11-16, 18-22, 23, 24-39, 77, 78, 79-82, 84 and 85.

Measurement of Lipase Enzyme Activity Using a NaOH Titration Method

The inhibitory activity of the selected compounds to pancreatic lipase was measured in the assay described in Pasquier et al; 1996, Vol 7, *Nutritional Biochemistry*, 293-302.

Log dose/response curves were constructed using a range of inhibitor concentrations.

Results

Selected benzoxazinone compounds were tested in the NaOH titration assay. In this assay, the activity of porcine pancreatic lipase in a system containing lipid micelles is recorded. These conditions are therefore similar to those encountered in the gastrointestinal tract.

A range of inhibitory activities were observed for the tested benzoxazinone compounds in this assay, indicating that these compounds are inhibitors of porcine pancreatic lipase. The following compounds had $IC_{50}$'s of $\leq 1$ µM:

Compounds 1, 2, 4, 6-9, 11-16, 18, 22-25, 27-36, 37-39, 78, 82, 84 and 85.

The results demonstrate that a number of selected benzoxazinones are inhibitors of fat digestion and that these compounds may be particularly suitable for the treatment of obesity.

Measurement of Trypsin Activity

Porcine trypsin (Boehringer) was dissolved at a concentration of 1 mg/ml in 100 mM MOPS (3-[N-Morpholino]propanesulphonic acid) pH 7.3 containing 2 mM $CaCl_2$. Prior to use, the enzyme was diluted 500 times to give a final concentration of 2 µg/ml.

Selected compounds were routinely stored as 5 mM stock solutions dissolved in DMSO (Dimethylsulphoxide) at −20° C. For the assay, aliquots were defrosted and a series of dilutions (×100, ×200, ×1,000, ×2,000, ×10,000, ×20,000 and ×100,000) made in 100 mM MOPS pH 7.3 containing 2 mM $CaCl_2$. The substrate Bz-Phe-Val-Arg-pNA (Benzoyl-phenylalanyl-valyl-arginine-p-nitroanilide) was dissolved in DMSO to give a 10 mM solution. Immediately prior to use, the substrate was diluted to 0.3 mM (30 µl/ml) in 100 mM MOPS containing 2 mM $CaCl_2$.

The assay was set up in triplicate in a 96 well ELISA plate. 10 µl 2 µg/ml trypsin, 26 µl diluted inhibitor and 190 µl substrate were added sequentially. The plates were then incubated at 37° C. in a BioRad Benchmark Microplate Reader. The rate of release of p-nitroaniline was measured at 405 nm over 10 minutes relative to that of the enzyme without inhibitor.

Measurement of Chymotrypsin Activity

Bovine Chymotrypsin (Sigma Type 11 Cat. No. C4129) was dissolved at a concentration of 1 mg/ml in 100 mM Tris pH 7.8. Prior to use, the enzyme was diluted 20 fold immediately before use, with the same buffer.

Selected compounds were routinely stored as 5 mM stock solutions dissolved in DMSO (Dimethylsulphoxide) at −20° C. For the assay, aliquots were defrosted and a series of dilutions (×20, ×100, ×200, ×1,000, ×2,000, ×10,000, ×20, 000 and ×100,000) made in 100 mM Tris pH 7.8. The substrate H-Ala-Ala-Phe-p-nitroanilide (H-alanyl-alanyl-phenylalanine-p-nitroanilide) (Bachem Cat. No. L-1095) was dissolved in DMSO to give a 10 mM stock and stored at 4° C. until use. Immediately prior to use, the substrate was diluted to 0.3 mM final concentration (30 µl/ml) just before use.

The assay was set up in triplicate in a 96 well ELISA plate. 10 µl 50 µg/ml chymotrypsin, 50 µl diluted inhibitor and 190 µl substrate were added sequentially. The plates were then incubated at 37° C. in a BioRad Benchmark Microplate Reader. The rate of release of p-nitroaniline was measured at 405 nm over 10 minutes relative to that of the enzyme without inhibitor.

Results

The selectivity of compound 18 towards human pancreatic lipase, trypsin and chymotrypsin was measured in the assays described above. The inhibitory activity of compound 18 towards lipase was assessed in the quinine diimine dye colorimetric assay.

At 500 nM compound 18 had inhibited 98.7% of the pancreatic lipase activity but only 4% of the trypsin activity and 12.5% of the chymotrypsin activity. Thus compound 18 is a highly selective lipase inhibitor.

Mouse Model Assay

Compound 18 was assayed in a mouse model as described by Isler et al., *British Journal of Nutrition*, 1995, 73:851-862 and was found to be a potent lipase inhibitor.

Synthesis of Intermediates

Synthesis of 4-Substituted Anthranilic Acids

Example: 4-octyl Anthranilic Acid (4-octyl-2-Aminobenzoic Acid)

Method based on that of L. A. Paquette et al. J.Am.Chem. Soc. 99, 3734 (1981)

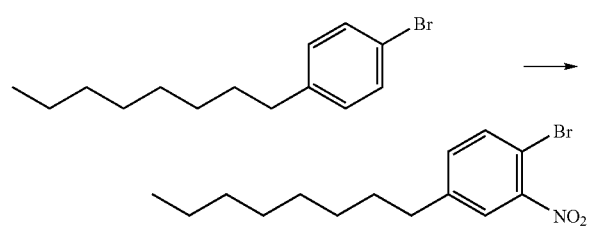

A solution of 1-bromo-4-octylbenzene (9.9 g, 36 mmol) in sulfuric acid (20 ml) was cooled in an ice bath. To this was added nitric acid (1.44 ml, 36 mmol). The ice bath was removed and the mixture stirred at room temperature for 20 minutes. A further portion of nitric acid was added (0.07 ml, 1.75 mmol), stirring being continued for a further 20 min. The mixture was poured into aqueous potassium carbonate, which was extracted with ethyl acetate. The organic extract was washed with saturated aqueous potassium carbonate, water and brine then dried (MgSO$_4$) and concentrated. Purification of the crude product by flash chromatography (1% EtOAc/hexane) removed the unwanted (major) regioisomer and afforded the desired material as a yellow oil (1.7 g, 5.4 mmol).

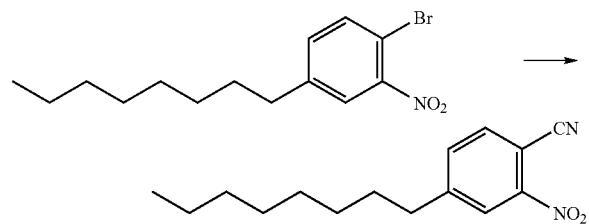

The substrate (1.7 g, 5.4 mmol), copper (I) cyanide (0.533 g, 5.9 mmol) and pyridine (20 ml) were refluxed at 150° C. for 2 days. Concentration in vacuo and purification by flash chromatography (10% to 20% EtOAc/hexane) gave the desired material as a brown oil (739 mg, 2.8 mmol)

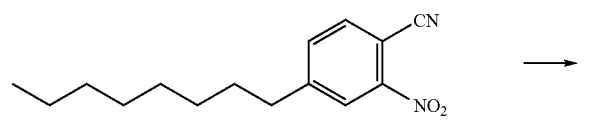

-continued

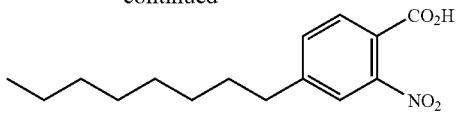

The substrate (694 mg, 2.7 mmol) was heated at 150° C. in a mixture of water (2 ml), AcOH (1 ml) and sulfuric acid (1 ml) for 2 days. The mixture was extracted with ethyl acetate, the organic phase being washed with water (×2), dried (Na$_2$SO$_4$) and concentrated to give the desired material (744 mg, 2.7 mmol).

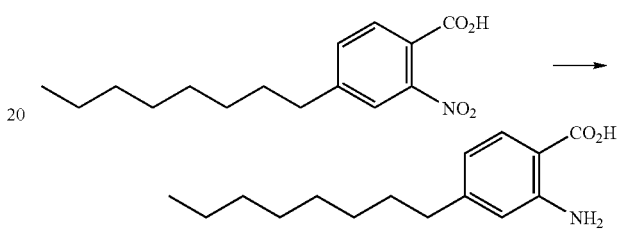

The starting material (744 mg, 2.7 mmol) was dissolved in ethanol (10 ml) and to this was added a slurry of 10% palladium on charcoal (40 mg) in ethanol (4 ml). The flask was flushed with nitrogen then hydrogen (1 atm) after which stirring was maintained overnight. Further portions of catalyst (5 mg and 25 mg) were added, the reaction being complete after a further 24 h. The reaction mixture was filtered through celite, thoroughly rinsing with methanol and ethyl acetate. Concentration gave the anthranilic acid (597 mg, 2.4 mmol) of sufficient purity for use without further purification; $\delta_H$ (400 MHz, CDCl$_3$) 0.79-0.81 (3H, m, Me), 1.12-1.36 (10H, m, 5×CH$_2$), 1.52 (2H, br.s, ArCH$_2$CH$_2$), 2.45 (2H, br.s, ArCH$_2$), 6.42 (2H, br.s, 2×ArH), 7.74 (1H, br.s, ArH); m/z (ES$^+$) 250 (MH$^+$).

Synthesis of 5-Substituted Anthranilic Acids

Example: 5-octyl Anthranilic Acid

Method based on that of B. R. Baker et al. J.Org.Chem 17, 141 (1952)

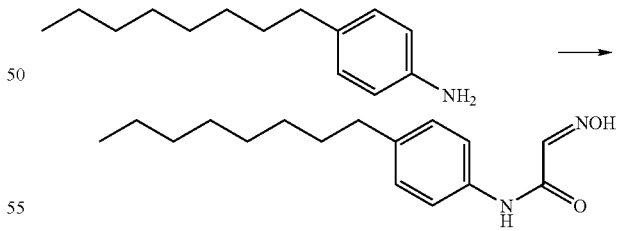

Chloral hydrate (3.97 g, 24 mmol) was dissolved in water (50 ml). To this solution was added, sequentially, anhydrous sodium sulfate (5.5 g, 39 mmol), 4-octylaniline (5 ml, 22 mmol), water (15 ml), concentrated hydrochloric acid (2.3 ml) and an aqueous solution of hydroxylamine hydrochloride (4.5 g in 22 ml, 65 mmol). The heterogeneous mixture was heated to 95° C. for 2 h, then 101° C. for a further 1 h. The reaction mixture was cooled to room temperature, the brown precipitate filtered and washed with water. This was dissolved in dichloromethane, dried (MgSO$_4$) and concentrated to give 5.6 g of crude material which was purified by flash chromatography on silica (20% EtOAc/hexane) to afford the desired material (2 g, 7.2 mmol).

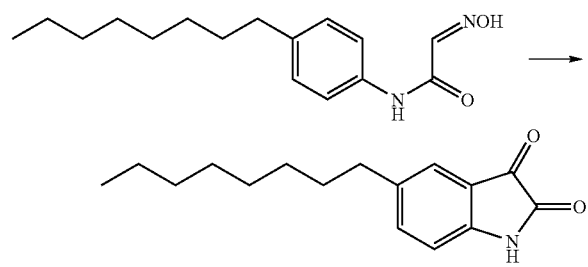

The oxime (1.8 g, 6.5 mmol) was added to a mixture of conc. sulfuric acid (13 ml) and water (1 ml) at 60° C. over the course of 15 min. The mixture was then heated to 80° C. for 2 h then stood at room temperature overnight. This was then extracted with ethyl acetate (×3), the combined organic layers being washed with saturated aqueous sodium bicarbonate and water until the washings were neutral. The organic phase was dried (MgSO$_4$) and concentrated to give the isatin as a red solid (1.5 g, 5.8 mmol), which was used without further purification.

A mixture of the isatin (1.5 g, 5.8 mmol) and 1.5M sodium hydroxide (13 ml) was warmed to 50° C. The heat was removed and a solution of 35% aqueous hydrogen peroxide (1.5 ml) was added, at a rate that maintained the temperature at 50-55° C. The reaction was then allowed to cool and stirred at room temperature for 30 min. Acidification to pH 2 with concentrated hydrochloric acid caused the product to precipitate. The liquid was decanted off, the solid being washed with water. The solid was partitioned between water and dichloromethane, the organic phase being washed with brine, dried (MgSO$_4$) and concentrated to give the desired anthranilic acid (1.4 g, 5.6 mmol). No further purification was required: δ(400 MHz, CDCl$_3$) 0.81 (3H, t, J 6.6, Me), 1.20-1.23 (10H, m, 5×CH$_2$), 1.49 (2H, br.s, ArCH$_2$CH$_2$), 2.41-2.44 (2H, m, ArCH$_2$), 6.55 (1H, d, J 8.3, ArH), 7.09 (1H, d, J 8.3, ArH), 7.65 (1H, s, ArH); m/z (ES$^+$) 250 (MH$^+$).

Preparation of Aryl Chloroformates:
Example: 4-Phenoxyphenylchloroformate

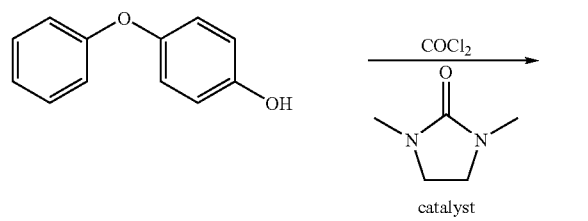

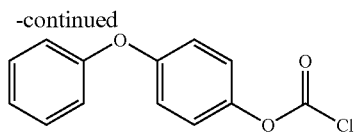

4-Phenoxyphenol (1.68 g, 9 mmol), 1,4-dimethylimidazolidin-2-one (0.051 ml, 0.45 mmol) and phosgene solution (4.5 ml of a 20% solution in toluene, 9 mmol) were heated to 40° C. for 30 min. The temperature was then increased to 80° C., and five further portions of phosgene solution (2.25 ml each, 4.5 mmol) were added at 30 min intervals. 30 min after the last addition, the solution was allowed to cool to r.t. and stand overnight. An aliquot was added to MeOH/pyridine to form the stable methyl carbamate, whereupon tlc (10% EtOAc/hexane) showed almost complete disappearance of starting material. The chloroformate solution was used directly in the preparation of compound 29, using the procedure described in Example 4 below.

Synthesis of Novel Compounds According to the Invention

EXAMPLE 1

6-Methyl-2-octyloxy-4H-3,1-benzoxazin-4-one
(Reference Number 11)

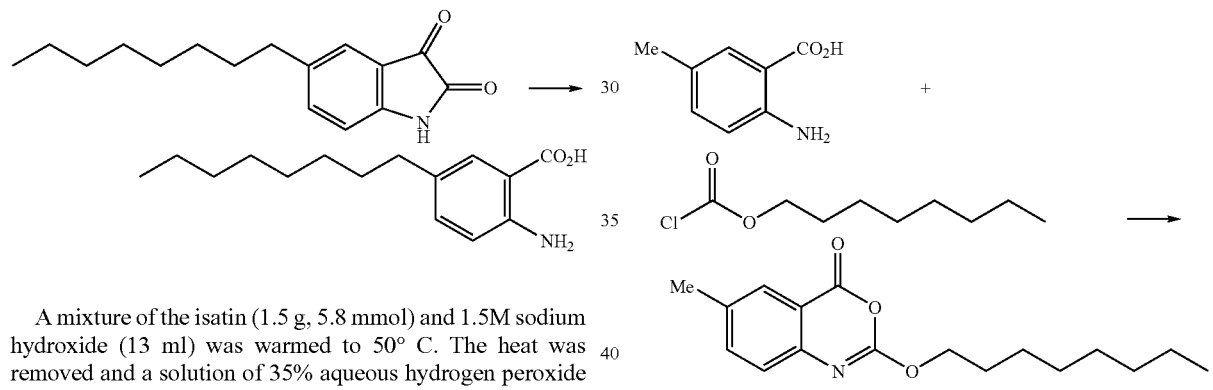

A solution of 2-amino-5-methylbenzoic acid (302 mg, 2 mmol) in pyridine (10 ml) was cooled to 0° C. and treated dropwise with octyl chloroformate (1.15 ml, 6 mmol). The resulting mixture was allowed to warm to room temperature and stirred for 4 h. The pyridine was removed under vacuum and the residue dissolved in ethyl acetate (50 ml). This solution was washed with 1M HCl (10 ml) and brine (5 ml), dried (MgSO$_4$) and the solvent removed in vacuo to afford a pale orange oily solid. Recrystallisation from hexane afforded the desired product as an off-white solid (144 mg, 25%); δ$_H$ (400 MHz, DMSO-d$_6$) 0.68 (3H, t, J 7, CH$_2$CH$_3$), 1.26-1.40 (10H, m, 5×CH$_2$), 1.73 (2H, tt, J. J' 7, OCH$_2$CH$_2$), 2.35 (3H, s, CH$_3$), 4.35 (2H, t, J 7, OCH$_2$), 7.34 (1H, d, J 8, Ph), 7.65 (1H, d, J 8, Ph), 7.83 (1H, s, Ph); m/z (ES$^+$) 290 (MH$^+$).

EXAMPLE 2

6-Methyl-2-phenoxy-4H-3,1-benzoxazin-4-one
(Reference Number 8)

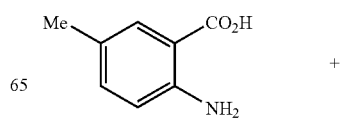

-continued

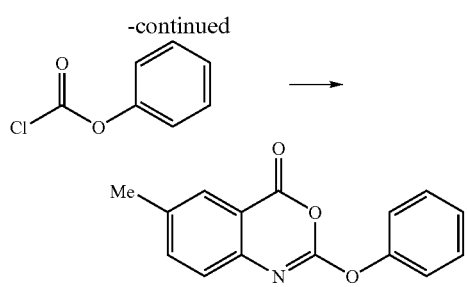

A solution of 2-amino-5-methylbenzoic acid (1.0 g, 6.6 mmol) in pyridine (10 ml) was cooled to 0° C. and treated dropwise with phenyl chloroformate (3.3 ml, 26 mmol). The resulting mixture was allowed to warm to room temperature and stirred for 16 h, after which time the pyridine was removed in vacuo. The residue was washed with water (20 ml) and dried in vacuo. Recrystallisation from toluene afforded the desired product as a pale brown solid (692 mg, 41%); $\delta_H$ (400 MHz, DMSO-$d_6$) 2.40 (3H, s, $CH_3$), 7.33-7.45 (3H, m, Ph), 7.48-7.55 (3H, m, Ph), 7.63 (1H, d, J 8, Ph), 7.89 (1H, s, Ph-H5); m/z ($ES^+$) 254 ($MH^+$).

EXAMPLE 3

2-Propoxy-6-methyl-4H-3,1-benzoxazin-4-one
(Reference Number 9)

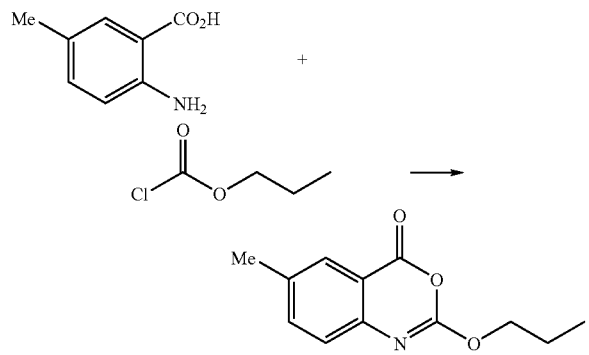

A solution of 2-amino-5-methylbenzoic acid (1.0 g, 6.6 mmol) in pyridine (10 ml) was cooled to 0° C. and treated dropwise with propyl chloroformate (3.0 ml, 26 mmol). The resulting mixture was allowed to warm to room temperature and stirred for 4 h, after which time the pyridine was removed in vacuo. The residue was washed with water (25 ml) and dried in vacuo to afford the desired product as an off-white solid (0.96 g, 66%); 5H (400 MHz, DMSO-$d_6$) 1.03 (3H, t, J 7, $CH_2CH_3$), 1.82 (2H, tq, J, J' 7, $CH_2CH_3$), 2.46 (3H, s, $CH_3$), 4.42 (2H, t, J 7, $OCH_2$), 7.40 (1H, d, J 8, Ph), 7.71 (1H, d, J 8, Ph), 7.89 (1H, s, Ph); m/z ($ES^+$) 219 ($MH^+$).

EXAMPLE 4

2-Hexadecyloxy-6-methyl-4H-3,1-benzoxazin-4-one
(Compound 18)

Preparation 1

Step 1:

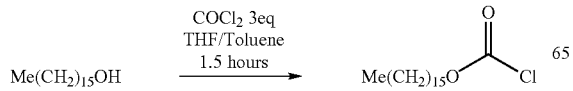

1-Hexadecanol (0.78 g, 3.2 mmol, 1 eq.) was dissolved in the minimum amount of THF under nitrogen. To this was added a 20% solution of phosgene in toluene (2.34 ml, 5 mmol, 1.5 eq.). After 45 minutes, a second similar portion of phosgene solution was added. After a further 45 minutes, the apparatus was purged with nitrogen (scrubbed on exit with 5M sodium hydroxide) to remove excess phosgene.

Step 2:

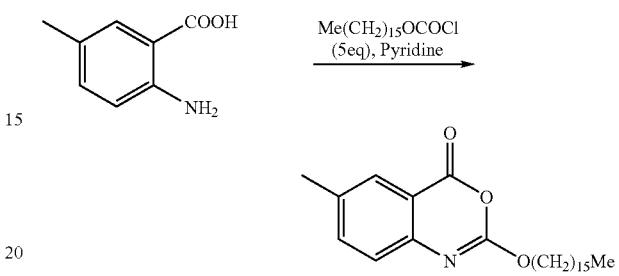

2-Amino-5-methylbenzoic acid (100 mg, 0.64 mmol, 0.2 eq.) was dissolved in pyridine (10 ml). The chloroformate solution was added dropwise by syringe and the mixture stirred at room temperature for 2 hours. The mixture was diluted with ethyl acetate (100 ml) and washed with 10% aqueous citric acid (100 ml, ×2), saturated sodium bicarbonate solution (100 ml, ×2), water (100 ml) and saturated brine (100 ml). The organic phase was dried ($MgSO_4$) and concentrated in vacuo.

The residue was purified by flash chromatography on silica, eluting with 1:5:94 diisopropylethylamine/ethyl acetate/hexane to afford a white solid (40 mg, 15%) $\delta$(400 MHz, $CDCl_3$) 0.87 (3H, t, J 6.8, $CH_2CH_3$), 1.24-1.45 (26H, m, 13×$CH_2$), 1.75-1.83 (2H, m, $OCH_2CH_2$), 2.41 (3H, s, $ArCH_3$), 4.41 (2H, t, J 6.7, $OCH_2$), 7.30 (1H, d, J 8.3, ArH), 7.51 (1H, dd, J 8.5, 2.0, ArH), 7.90 (1H, d, J 1.1, ArH); m/z ($ES^+$) 402 ($MH^+$); MPt. 72-73° C.

Thin layer chromatograms (solvent 1% diisopropylamine/ 5% ethyl acetate/94% hexane) were visualised with UV and phosphomolybdic acid in ethanol ($R_f$ (compound 18)=0.6).

Preparation 2

Step 1:

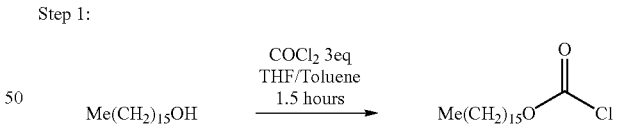

1-Hexadecanol (5.01 g, 20.6 mmol, 1 eq.) was dissolved in THF (10 ml) under nitrogen and added to a 20% solution of phosgene in toluene (29 ml, 62.5 mmol, 3 eq.). The mixture was stirred at room temperature for 2 hours, then the apparatus was purged with nitrogen (scrubbed on exit with 5M sodium hydroxide) to remove excess phosgene.

Step 2:

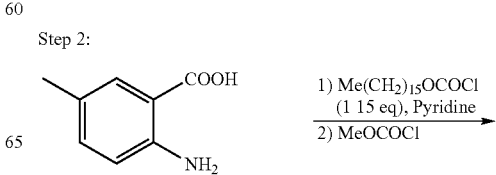

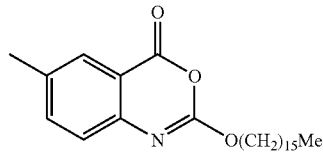

2-Amino-5-methylbenzoic acid (2.71 g, 17.9 mmol, 0.87 eq.) was dissolved in pyridine (24 ml) and added to the chloroformate solution prepared above. The mixture was stirred at room temperature for 1.75 hours. Methyl chloroformate (13.6 ml, 176 mmol, 8.5 eq) was added slowly, then the mixture was left to stir at ambient temperature overnight. The mixture was diluted with ethyl acetate (20 ml) and washed with water (15 ml) and 10% aqueous citric acid (20 ml). The combined aqueous phases were extracted with ethyl acetate (20 ml). The organic extracts were combined and washed with water (20 ml) and brine (20 ml) then concentrated to give a solid. This was slurried in pentane (5 ml), filtered, then slurried in acetonitrile (5 ml), filtered and purified by flash chromatography on silica (1.5% diisopropylethylamine in dichloromethane) to give a white solid (2.51 g, 31%) $\delta_H$ (400 MHz, CDCl$_3$) 0.87 (3H, t, J 6.8, CH$_2$CH$_3$), 1.24-1.45 (26H, m, 13×CH$_2$), 1.75-1.83 (2H, m, OCH$_2$CH$_2$), 2.41 (3H, s, ArCH$_3$), 4.41 (2H, t, J 6.7, OCH$_2$), 7.30 (1H, d, J 8.3, ArH), 7.51 (1H, dd, J 8.5, 2.0, ArH), 7.90 (1H, d, J 1.1, ArH); m/z (ES$^+$) 402 (MH$^+$); MPt. 72-73° C.

EXAMPLE 5

The other compounds listed in Table 1 may be prepared in a similar manner to Examples 1 to 4 above, in particular the following compounds were prepared using the starting materials indicated:

| Compound number | Starting material 1 | Starting material 2 |
|---|---|---|
| 4 | 2-aminobenzoic acid | 4-methylphenyl chloroformate |
| 5 | 2-aminobenzoic acid | 4-chlorophenyl chloroformate |
| 8 | 2-amino-5-methylbenzoic acid | phenyl chloroformate |
| 10 | 2-aminobenzoic acid | 2-ethylhexyl chloroformate |
| 11 | 2-amino-5-methylbenzoic acid | octyl chloroformate |
| 12 | 2-amino-5-methylbenzoic acid | hexyl chloroformate |
| 13 | 2-amino-5-methylbenzoic acid | 2-ethylhexyl chloroformate |
| 14 | 2-amino-5-ethylbenzoic acid | hexyl chloroformate |
| 15 | 2-amino-5-methylbenzoic acid | Decanol |
| 16 | 2-amino-5-methylbenzoic acid | 1-tetradecanol |
| 17 | 2-amino-5-methylbenzoic acid | 1-pentadecanol |
| 19 | 2-amino-5-methylbenzoic acid | 1-heptadecanol |
| 20 | 2-amino-5-methylbenzoic acid | 1-octadecanol |
| 21 | 4-ethyl-2-aminobenzoic acid | Hexyl chloroformate |
| 22 | 5-methyl-2-aminobenzoic acid | 3,7-dimethyloctan-1-ol |
| 23 | 5-methyl-2-aminobenzoic acid | 2-(2-hexyloxyethoxy)ethanol |
| 24 | 5-methyl-2-aminobenzoic acid | Z-9-octadecen-1-ol |
| 25 | 5-methyl-2-aminobenzoic acid | 10-phenyldecan-1-ol |
| 26 | 4-ethyl-2-aminobenzoic acid | Octyl chloroformate |
| 27 | 2-aminobenzoic acid | Octyl chloroformate |
| 28 | 5-methoxy-2-aminobenzoic acid | Octyl chloroformate |
| 29 | 5-methyl-2-aminobenzoic acid | 4-phenoxyphenol |
| 30 | 2-aminobenzoic acid | Hexyl chloroformate |
| 31 | 2-aminobenzoic acid | 1-dodecanol |
| 32 | 5-iodo-2-aminobenzoic acid | Octyl chloroformate |
| 33 | 4-butyl-2-aminobenzoic acid | Octyl chloroformate |
| 34 | 5-methyl-2-aminobenzoic acid | 8-phenyloctan-1-ol |
| 35 | 5-methyl-2-aminobenzoic acid | 4-phenylbutan-1-ol |
| 36 | 5-methyl-2-aminobenzoic acid | 12-phenyldodecan-1-ol |
| 37 | 5-methyl-2-aminobenzoic acid | Z-11-octadecen-1-ol |
| 38 | 5-methyl-2-aminobenzoic acid | 11-octadecyn-1-ol |
| 39 | 5-methyl-2-aminobenzoic acid | 10-(2-thienyl)decan-1-ol |
| 78 | 6-methyl-2-aminobenzoic acid | Octyl chloroformate |
| 79 | 4-octyl-2-aminobenzoic acid | Octyl chloroformate |
| 80 | 5-octyl-2-aminobenzoic acid | Octyl chloroformate |
| 81 | 5-methyl-2-aminobenzoic acid | 5-chloropentan-1-ol |
| 82 | 2-amino-5-methylbenzoic acid | 1,16-hexadecandiol |
| 83 | 3,5-dimethyl-2-aminobenzoic acid | Octyl chloroformate |
| 84 | 2-amino-5-methylbenzoic acid | 6-phenoxyhexan-1-ol |
| 85 | 2-amino-5-methylbenzoic acid | 6-(4-phenoxyphenoxy)hexan-1-ol |

The foregoing description details specific compounds, compositions, methods and uses which can be employed to practice the present invention. However, those skilled in the art will know how to use alternative reliable methods for aiming at alternative embodiments of the invention which are herein encompassed.

What is claimed is:

1. A method for the treatment of obesity or an obesity-related disorder selected from the group consisting of hyperlipaemia, hyperlipidaemia, hyperglycaemia (type II diabetes), hypertension, cardiovascular disease, stroke, and gastrointestinal disease, the method comprising administering to a subject in need thereof a therapeutically effective amount of a compound of formula (II):

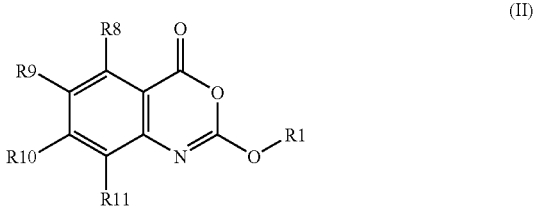

(II)

or a pharmaceutically acceptable salt, ester or amide thereof, wherein:

R$^1$ is a branched or unbranched alkyl which is optionally interrupted by one or more oxygen atoms, alkenyl, alkynyl, phenyl, phenylalkyl, or a substituted derivative of any of the foregoing groups, wherein the substituents are one or more independently of halogen, alkyl, or —OR$^6$, and wherein when R$^1$ is a branched or unbranched alkyl it can also be optionally substituted with phenyl, thienyl or benzoxazin-4-one, with the proviso that any hetero atom substituent in R$^1$ must be separated from the exocyclic oxygen atom by at least two carbon atoms;

R$^6$ is alkyl or phenyl; and

R$^8$, R$^9$, R$^{10}$, R$^{11}$ are each independently hydrogen, halo, hydroxyl, alkyl, or alkoxy.

2. The method of claim 1, wherein in the compound of formula (II), R$^1$ is either a branched or unbranched alkyl group having up to 25 carbon atoms optionally substituted with —OR$^6$; a phenyl group optionally substituted with —OR$^6$; or a phenylalkyl group wherein the alkyl moiety has up to 25 carbon atoms;

R$^8$ is hydrogen or fluorine;

R$^9$ is lower branched or unbranched alkyl having 1 to 10 carbon atoms; or a halogen R$^{10}$ is hydrogen, lower branched or unbranched alkyl having 1 to 10 carbon atoms; or a halogen and R[11] is hydrogen, lower branched or unbranched alkyl having 1 to 10 carbon atoms or a halogen.

3. The method of claim 1, wherein the step of administering the compound to a subject comprises administering the compound to a human.

4. The method of claim 1, wherein the step of administering the compound to a subject comprises administering the compound to an animal.

5. The method of claim 1 with the proviso that in the definition of R[1], any hetero atom substituent in R[1] must be separated from the exocyclic oxygen atom by at least two saturated carbon atoms.

6. The method of claim 1, wherein the method is for the treatment of obesity.

7. The method of claim 1, wherein the method is for the treatment of an obesity related disorder selected from the group consisting of hyperlipaemia, hyperlipidaemia, hyperglycaemia (type II diabetes), hypertension, cardiovascular disease, stroke, and gastrointestinal disease.

8. A method for treatment of obesity or an obesity-related disorder selected from the group consisting of hyperlipaemia, hyperlipidaemia, hyperglycaemia (type II diabetes), hypertension, cardiovascular disease, stroke, and gastrointestinal disease, the method comprising administering to a subject in need thereof a therapeutically effective amount of a compound selected from:
  2-Ethoxy-6-methyl-4H-3,1-benzoxazin-4-one;
  2-Phenoxy-4H-3,1-benzoxazin-4-one;
  2-(4-Methylphenoxy)-4H-3,1-benzoxazin-4-one;
  2-(4-Chlorophenoxy)-4H-3,1-benzoxazin-4-one;
  2-(2-Chloroethoxy)-4H-3,1-benzoxazin-4-one;
  2-Propoxy-4H-3,1-benzoxazin-4-one;
  6-Methyl-2-phenoxy-4H-3,1-benzoxazin-4-one;
  6-Methyl-2-propoxy-4H-3,1-benzoxazin-4-one;
  2-(2-Ethylhexyloxy)-4H-3,1-benzoxazin-4-one;
  6-Methyl-2-octyloxy-4H-3,1-benzoxazin-4-one;
  2-Hexyloxy-6-methyl-4H-3,1-benzoxazin-4-one;
  2-(2-Ethylhexyloxy)-6-methyl-4H-3,1-benzoxazin-4-one;
  6-Ethyl-2-hexyloxy-4H-3,1-benzoxazin-4-one;
  2-Decyloxy-6-methyl-4H-3,1-benzoxazin-4-one;
  6-Methyl-2-tetradecyloxy-4H-3,1-benzoxazin-4-one;
  6-Methyl-2-pentadecyloxy-4H-3,1-benzoxazin-4-one;
  2-Hexadecyloxy-6-methyl-4H-3,1-benzoxazin-4-one;
  2-Heptadecyloxy-6-methyl-4H-3,1-benzoxazin-4-one;
  6-Methyl-2-octadecyloxy-4H-3,1-benzoxazin-4-one;
  7-Ethyl-2-hexyloxy-4H-3,1-benzoxazin-4-one;
  2-(3,7-Dimethyloctyloxy)-6-methyl-4H-3,1-benzoxazin-4-one;
  2-[2-(2-Hexyloxyethoxy)ethoxy]-6-methyl-4H-3,1-benzoxazin-4-one;
  (Z)-6-Methyl-2-(octadeca-9-enyloxy)-4H-3,1-benzoxazin-4-one;
  6-Methyl-2-(10-phenyldecyloxy)-4H-3,1-benzoxazin-4-one;
  7-Ethyl-2-octyloxy-4H-3,1-benzoxazin-4-one;
  2-Octyloxy-4H-3,1-benzoxazin-4-one;
  6-Methoxy-2-octyloxy-4H-3,1-benzoxazin-4-one;
  6-Methyl-2-(4-phenoxyphenoxy)-4H-3,1-benzoxazin-4-one;
  2-Hexyloxy-4H-3,1-benzoxazin-4-one;
  2-Dodecyloxy-6-methyl-4H-3,1-benzoxazin-4-one;
  6-Iodo-2-octyloxy-4H-3,1-benzoxazin-4-one;
  7-Butyl-2-Octyloxy-4H-3,1-benzoxazin-4-one;
  6-Methyl-2-(8-phenyloctyloxy)-4H-3,1-benzoxazin-4-one;
  6-Methyl-2-(4-phenylbutyloxy)-4H-3,1-benzoxazin-4-one;
  6-Methyl-2-(12-phenyldodecyloxy)-4H-3,1-benzoxazin-4-one;
  (Z)-6-Methyl-2-(octadeca-11-enyloxy)-4H-3,1-benzoxazin-4-one;
  6-Methyl-2-(octadeca-11-ynyloxy)-4H-3,1-benzoxazin-4-one;
  6-Methyl-2-[-10-(thien-2-yl)-decyloxy]-4H-3,1-benzoxazin-4-one;
  2-Hexadecyloxy-6,7-dimethyl-4H-3,1-benzoxazin-4-one;
  5-Methyl-2-octyloxy-4H-3,1-benzoxazin-4-one;
  7-Octyl-2-octyloxy-4H-3,1-benzoxazin-4-one;
  6-Octyl-2-octyloxy-4H-3,1-benzoxazin-4-one;
  2-(5-Chloropentyloxy)-6-methyl-4H-3,1-benzoxazin-4-one;
  2,2'-(1,16-Hexadecylidenedioxy)-bis-4H-3,1-benzoxazin-4-one;
  6-Methyl-2-(6-phenoxyhexyloxy)-4H-3,1-benzoxazin-4-one;
  6-Methyl-2-[6-(4-phenoxyphenoxy)hexyloxy]-4H-3,1-benzoxazin-4-one;
  or a pharmaceutically acceptable salt, ester, or amide thereof.

9. The method of claim 8, wherein the compound is selected from:
  2-(4-Methylphenoxy)-4H-3,1-benzoxazin-4-one;
  2-(4-Chlorophenoxy)-4H-3,1-benzoxazin-4-one;
  6-Methyl-2-phenoxy-4H-3,1-benzoxazin-4-one;
  2-(2-Ethylhexyloxy)-4H-3,1-benzoxazin-4-one;
  6-Methyl-2-octyloxy-4H-3,1-benzoxazin-4-one;
  2-Hexyloxy-6-methyl-4H-3,1-benzoxazin-4-one;
  2-(2-Ethylhexyloxy)-6-methyl-4H-3,1-benzoxazin-4-one;
  6-Ethyl-2-hexyloxy-4H-3,1-benzoxazin-4-one;
  7-Ethyl-2-hexyloxy-4H-3,1-benzoxazin-4-one;
  7-Ethyl-2-octyloxy-4H-3,1-benzoxazin-4-one;
  2-Octyloxy-4H-3,1-benzoxazin-4-one;
  6-Methoxy-2-octyloxy-4H-3,1-benzoxazin-4-one;
  2-Hexyloxy-4H-3,1-benzoxazin-4-one;
  6-Iodo-2-octyloxy-4H-3,1-benzoxazin-4-one;
  7-Butyl-2-Octyloxy-4H-3,1-benzoxazin-4-one;
  6-Methyl-2-(8-phenyloctyloxy)-4H-3,1-benzoxazin-4-one;
  6-Methyl-2-(4-phenylbutyloxy)-4H-3,1-benzoxazin-4-one;
  5-Methyl-2-octyloxy-4H-3,1-benzoxazin-4-one;
  or a pharmaceutically acceptable salt, ester, or amide thereof.

10. The method of claim 8, wherein the compound is selected from:
  2-Decyloxy-6-methyl-4H-3,1-benzoxazin-4-one;
  6-Methyl-2-tetradecyloxy-4H-3,1-benzoxazin-4-one;
  6-Methyl-2-pentadecyloxy-4H-3,1-benzoxazin-4-one;
  2-Hexadecyloxy-6-methyl-4H-3,1-benzoxazin-4-one;
  2-Heptadecyloxy-6-methyl-4H-3,1-benzoxazin-4-one;
  6-Methyl-2-octadecyloxy-4H-3,1-benzoxazin-4-one;
  2-(3,7-Dimethyloctyloxy)-6-methyl-4H-3,1-benzoxazin-4-one;
  2-[2-(2-Hexyloxyethoxy)ethoxy]-6-methyl-4H-3,1-benzoxazin-4-one;
  (Z)-6-Methyl-2-(octadeca-9-enyloxy)-4H-3,1-benzoxazin-4-one;
  6-Methyl-2-(10-phenyldecyloxy)-4H-3,1-benzoxazin-4-one;
  6-Methyl-2-(4-phenoxyphenoxy)-4H-3,1-benzoxazin-4-one;

2-Dodecyloxy-6-methyl-4H-3,1-benzoxazin-4-one;
6-Methyl-2-(12-phenyldodecyloxy)-4H-3,1-benzoxazin-4-one;
(Z)-6-Methyl-2-(octadeca-11-enyloxy)-4H-3,1-benzoxazin-4-one;
6-Methyl-2-(octadeca-11-ynyloxy)-4H-3,1-benzoxazin-4-one;
6-Methyl-2-[-10-(thien-2-yl)-decyloxy]-4H-3,1-benzoxazin-4-one;
7-Octyl-2-octyloxy-4H-3,1-benzoxazin-4-one;
6-Octyl-2-octyloxy-4H-3,1-benzoxazin-4-one;
2-(5-Chloropentyloxy)-6-methyl-4H-3,1-benzoxazin-4-one;
2,2'-(1,16-Hexadecylidenedioxy)-bis-4H-3,1-benzoxazin-4-one;
6-Methyl-2-(6-phenoxyhexyloxy)-4H-3,1-benzoxazin-4-one;
6-Methyl-2-[6-(4-phenoxyphenoxy)hexyloxy]-4H-3,1-benzoxazin-4-one;
or a pharmaceutically acceptable salt, ester, or amide thereof.

11. The method of claim 8, wherein the compound is selected from:
6-Methyl-2-propoxy-4H-3,1-benzoxazin-4-one;
6-Methyl-2-octyloxy-4H-3,1-benzoxazin-4-one;
2-Hexyloxy-6-methyl-4H-3,1-benzoxazin-4-one;
2-(2-Ethylhexyloxy)-6-methyl-4H-3,1-benzoxazin-4-one;
6-Ethyl-2-hexyloxy-4H-3,1-benzoxazin-4-one;
2-Decyloxy-6-methyl-4H-3,1-benzoxazin-4-one;
6-Methyl-2-tetradecyloxy-4H-3,1-benzoxazin-4-one;
2-Hexadecyloxy-6-methyl-4H-3,1-benzoxazin-4-one;
2-Heptadecyloxy-6-methyl-4H-3,1-benzoxazin-4-one;
6-Methyl-2-octadecyloxy-4H-3,1-benzoxazin-4-one;
7-Ethyl-2-hexyloxy-4H-3,1-benzoxazin-4-one;
2-(3,7-Dimethyloctyloxy)-6-methyl-4H-3,1-benzoxazin-4-one;
2-[2-(2-Hexyloxyethoxy)ethoxy]-6-methyl-4H-3,1-benzoxazin-4-one;
(Z)-6-Methyl-2-(octadeca-9-enyloxy)-4H-3,1-benzoxazin-4-one;
6-Methyl-2-(10-phenyldecyloxy)-4H-3,1-benzoxazin-4-one;
7-Ethyl-2-octyloxy-4H-3,1-benzoxazin-4-one;
2-Octyloxy-4H-3,1-benzoxazin-4-one;
6-Methoxy-2-octyloxy-4H-3,1-benzoxazin-4-one;
6-Methyl-2-(4-phenoxyphenoxy)-4H-3,1-benzoxazin-4-one;
2-Hexyloxy-4H-3,1-benzoxazin-4-one;
2-Dodecyloxy-6-methyl-4H-3,1-benzoxazin-4-one;
6-Iodo-2-octyloxy-4H-3,1-benzoxazin-4-one;
7-Butyl-2-Octyloxy-4H-3,1-benzoxazin-4-one;
6-Methyl-2-(8-phenyloctyloxy)-4H-3,1-benzoxazin-4-one;
6-Methyl-2-(4-phenylbutyloxy)-4H-3,1-benzoxazin-4-one;
6-Methyl-2-(12-phenyldodecyloxy)-4H-3,1-benzoxazin-4-one;
(Z)-6-Methyl-2-(octadeca-11-enyloxy)-4H-3,1-benzoxazin-4-one;
6-Methyl-2-(octadeca-11-ynyloxy)-4H-3,1-benzoxazin-4-one;
6-Methyl-2-[-10-(thien-2-yl)-decyloxy]-4H-3,1-benzoxazin-4-one;
2-Hexadecyloxy-6,7-dimethyl-4H-3,1-benzoxazin-4-one;
5-Methyl-2-octyloxy-4H-3,1-benzoxazin-4-one;
7-Octyl-2-octyloxy-4H-3,1-benzoxazin-4-one;
6-Octyl-2-octyloxy-4H-3,1-benzoxazin-4-one;
2-(5-Chloropentyloxy)-6-methyl-4H-3,1-benzoxazin-4-one;
2,2'-(1,16-Hexadecylidenedioxy)-bis-4H-3,1-benzoxazin-4-one;
6-Methyl-2-(6-phenoxyhexyloxy)-4H-3,1-benzoxazin-4-one;
6-Methyl-2-[6-(4-phenoxyphenoxy)hexyloxy]-4H-3,1-benzoxazin-4-one;
or a pharmaceutically acceptable salt, ester, or amide thereof.

12. The method of claim 8, wherein the compound is selected from:
2-Ethoxy-6-methyl-4H-3,1-benzoxazin-4-one;
2-Phenoxy-4H-3,1-benzoxazin-4-one;
2-(4-Methylphenoxy)-4H-3,1-benzoxazin-4-one;
2-(2-Chloroethoxy)-4H-3,1-benzoxazin-4-one;
2-Propoxy-4H-3,1-benzoxazin-4-one;
6-Methyl-2-phenoxy-4H-3,1-benzoxazin-4-one;
6-Methyl-2-propoxy-4H-3,1-benzoxazin-4-one;
6-Methyl-2-octyloxy-4H-3,1-benzoxazin-4-one;
2-Hexyloxy-6-methyl-4H-3,1-benzoxazin-4-one;
2-(2-Ethylhexyloxy)-6-methyl-4H-3,1-benzoxazin-4-one;
6-Ethyl-2-hexyloxy-4H-3,1-benzoxazin-4-one;
2-Decyloxy-6-methyl-4H-3,1-benzoxazin-4-one;
6-Methyl-2-tetradecyloxy-4H-3,1-benzoxazin-4-one;
2-Hexadecyloxy-6-methyl-4H-3,1-benzoxazin-4-one;
2-(3,7-Dimethyloctyloxy)-6-methyl-4H-3,1-benzoxazin-4-one;
2-[2-(2-Hexyloxyethoxy)ethoxy]-6-methyl-4H-3,1-benzoxazin-4-one;
(Z)-6-Methyl-2-(octadeca-9-enyloxy)-4H-3,1-benzoxazin-4-one;
6-Methyl-2-(10-phenyldecyloxy)-4H-3,1-benzoxazin-4-one;
2-Octyloxy-4H-3,1-benzoxazin-4-one;
6-Methoxy-2-octyloxy-4H-3,1-benzoxazin-4-one;
6-Methyl-2-(4-phenoxyphenoxy)-4H-3,1-benzoxazin-4-one;
2-Hexyloxy-4H-3,1-benzoxazin-4-one;
2-Dodecyloxy-6-methyl-4H-3,1-benzoxazin-4-one;
6-Iodo-2-octyloxy-4H-3,1-benzoxazin-4-one;
7-Butyl-2-Octyloxy-4H-3,1-benzoxazin-4-one;
6-Methyl-2-(8-phenyloctyloxy)-4H-3,1-benzoxazin-4-one;
6-Methyl-2-(4-phenylbutyloxy)-4H-3,1-benzoxazin-4-one;
6-Methyl-2-(12-phenyldodecyloxy)-4H-3,1-benzoxazin-4-one;
(Z)-6-Methyl-2-(octadeca-11-enyloxy)-4H-3,1-benzoxazin-4-one;
6-Methyl-2-(octadeca-11-ynyloxy)-4H-3,1-benzoxazin-4-one;
6-Methyl-2-[-10-(thien-2-yl)-decyloxy]-4H-3,1-benzoxazin-4-one;
5-Methyl-2-octyloxy-4H-3,1-benzoxazin-4-one;
2,2'-(1,16-Hexadecylidenedioxy)-bis-4H-3,1-benzoxazin-4-one;
6-Methyl-2-(6-phenoxyhexyloxy)-4H-3,1-benzoxazin-4-one;
6-Methyl-2-[6-(4-phenoxyphenoxy)hexyloxy]-4H-3,1-benzoxazin-4-one;
or a pharmaceutically acceptable salt, ester, or amide thereof.

13. The method of claim 8, wherein the compound of formula (II) is 2-hexadecyloxy-6-methyl-4H-3,1-benzoxazin-4-one.

14. The method of claim 8, wherein the compound of formula (II) is 2-Decyloxy-6-methyl-4H-3,1-benzoxazin-4-one.

15. The method of claim 8, wherein the compound of formula (II) is 6-Methyl-2-tetradecyloxy-4H-3,1-benzoxazin-4-one.

16. The method of claim 8, wherein the method is for the treatment of obesity.

17. The method of claim 13, wherein the method is for the treatment of obesity.

18. The method of claim 14, wherein the method is for the treatment of obesity.

19. The method of claim 15, wherein the method is for the treatment of obesity.

20. The method of claim 8, wherein the method is for the treatment of an obesity related disorder selected from the group consisting of hyperlipaemia, hyperlipidaemia, hyperglycaemia (type II diabetes), hypertension, cardiovascular disease, stroke, and gastrointestinal disease.

21. The method of claim 13, wherein the method is for the treatment of an obesity related disorder selected from the group consisting of hyperlipaemia, hyperlipidaemia, hyperglycaemia (type II diabetes), hypertension, cardiovascular disease, stroke, and gastrointestinal disease.

22. The method of claim 14, wherein the method is for the treatment of an obesity related disorder selected from the group consisting of hyperlipaemia, hyperlipidaemia, hyperglycaemia (type II diabetes), hypertension, cardiovascular disease, stroke, and gastrointestinal disease.

23. The method of claim 15, wherein the method is for the treatment of an obesity related disorder selected from the group consisting of hyperlipaemia, hyperlipidaemia, hyperglycaemia (type II diabetes), hypertension, cardiovascular disease, stroke, and gastrointestinal disease.

* * * * *